(12) United States Patent
Ahring et al.

(10) Patent No.: US 6,555,350 B2
(45) Date of Patent: Apr. 29, 2003

(54) METHOD FOR PROCESSING LIGNOCELLULOSIC MATERIAL

(75) Inventors: Birgitte Kiær Ahring, Stakkeledet 27, DK-2970 Hørsholm (DK); Anne Belinda Thomsen, Roskilde (DK)

(73) Assignees: Forskningscenter Riso, Roekilde (DK); Birgitte Kiær Ahring, Horshølm (DK)

( * ) Notice: Subject to any disclaimer, the term of this patent is extended or adjusted under 35 U.S.C. 154(b) by 0 days.

(21) Appl. No.: 09/763,449

(22) PCT Filed: Feb. 19, 2001

(86) PCT No.: PCT/DK01/00114

§ 371 (c)(1),
(2), (4) Date: May 1, 2001

(87) PCT Pub. No.: WO01/60752

PCT Pub. Date: Aug. 23, 2001

(65) Prior Publication Data

US 2002/0192774 A1 Dec. 19, 2002

(30) Foreign Application Priority Data

Feb. 17, 2000 (DK) .......................................... 2000 00256
Mar. 15, 2000 (DK) .......................................... 2000 00427

(51) Int. Cl.[7] .............................. C12P 7/14; C12P 7/06; C12P 7/00
(52) U.S. Cl. ........................ 435/162; 435/161; 435/132
(58) Field of Search ................................ 435/162, 161, 435/157, 155, 132, 41

(56) References Cited

U.S. PATENT DOCUMENTS

| | | |
|---|---|---|
| 4,604,215 A | 8/1986 | McCorquodale |
| 4,966,850 A | 10/1990 | Yu et al. |
| 5,221,357 A | 6/1993 | Brink |
| 5,783,081 A | 7/1998 | Gaddy |
| 5,932,456 A | 8/1999 | Van Draanen et al. |

FOREIGN PATENT DOCUMENTS

| | | |
|---|---|---|
| DE | 19637909 | 3/1998 |
| GB | 706686 | 4/1954 |
| GB | 812832 | 5/1959 |
| GB | 2033366 | 5/1980 |
| WO | 83/03108 | 9/1983 |
| WO | 00/14120 | 3/2000 |

OTHER PUBLICATIONS

Applied Microbiology and Biotechnology "Effects of lipids on thermophilic anaerobic digestion and reduction of lipid inhibition upon addition of bentonite" 1990, pp. 469–472 Angellidaki, S. P. Petersen and B. K. Ahring.

"*Thermoanaerobacter mathranii* sp. nov., an ethanol–producing, extremly thermophilic anaerobic bacterium from a hot spring in iceland" Arch Microbiol (1997) 168: 114–119 Lise Larsen, Peter Nielsen, Birgette K. Ahring.

"Substrate Analysis of Forest and Agricultural Wastes" Federal Research Centre of Forestry and Forest Products, Hamburg, Germany Jürgen Puls.

"Steam Pretreatment of Lignocellulosic Residues" Unversity of British Colombia 270–2357 Main Mall, Vancouver, 73–91 J. N. Saddler, L.. P. Ramos and C. Breuil.

"Optimization Of Wet Oxidation Pretreatment Of Wheat Straw" Bioresource Technology 64 (1998) 139–151 Anette Skammelsen Schmidt & Anne Belinda Thomsen.

"Production of ethanol from wet oxidised wheat straw by *Thermoanaerobacter mathranii*" Bioresource Technology 68 (1999) 3–9 B.K. Ahring, D. Licht, A.. S. Schmidt, P. Sommer, A. B. Thomsen.

Industrial And Engineering Chemistry "Solubility of Hydrogen, Oxygen, Nitrogen and Helium in Water at Elevated Temperatures" vol. 44, May (1952) 1146–1151 H. A. Pray, C. E. Schweickert and B. H. Minnich.

Biotechnology and Bioengineering vol. 49, No. 3, 1996: 229–246 "Granular Sludge Formation in Upflow Anaerobic Slidge Blanket (UASB) Reactors" Jens E. Schmiidt and Birgitte K. Ahring.

Applied Microbiogy and Biotechnology vol. 38: (1993) 537–541 "Xylanolytic anaerobic thermphiles from Iceland hot–springs" Jacob Sonne–Hansen, Indra Mathrani, Birgitte K. Ahring.

"Pretreatment Of Wheat Straw And Conversion Of Xylose And Xylan To Ethanol By Thermophilic Anaerobic Bacteria" Bioresource Technology 58 (1996) 107–113 B. K. Ahring, K. Nielsen, A. B. Bjerre & A.S. Schmiidt.

"Pretreatment of Wheat Straw Using Combined Wet Oxidation and Alkaline Hydrolysis Resulting in Convertible Cellulose and Hemicellulose" Biotechnology and Bioengineering, vol. 49, pp. 568–577 (1996) Anne Belinda Bjerre, Anne Bjerre Olesen, Tomas Fernqvist, Annette Ploger and Anette Skammelsen Schmidt.

Communications to the Editor "Compact Automated Displacement Gas Metering System for Measurement of Low Gas Rates from Laboratory Fermentors" Biotechnology adn Bioengineering, vol. 39, pp. 351–353 (1992) I. Angelidaki, L. Ellegaard and B. K. Ahring.

Acetic acid—friend or foe in anaerobic batch conversion of glucose to ethanol by *Saccharomyces cerevisiae*? Chemical Engineering Science, vol. 52, No. 15, pp 2653–2659, 1997 Mohammad J. Taherzadeh, Claes Niklasson and Gunnar Liden.

International Search Report, issued Aug. 8, 2001 in PCT/DK 001/00114.

*Primary Examiner*—Jon P. Weber
(74) *Attorney, Agent, or Firm*—Hunton & Williams

(57) ABSTRACT

A method wherein lignocellulosic biomass materials are converted into combustible fuel products. In particular, the method is a continuous process, involving wet oxidation or steam explosion, for fermentatively converting such biomass materials into ethanol using a process design that permits all or part of the process water from the ethanol fermentation process to be recycled to reduce the consumption of process water. The effluent from the ethanol fermentation step may be subjected to an anaerobic fermentation step generating methane and a water effluent in which the amount of potentially inhibitory substances is at a sub-inhibitory level, which in turn permits all or part of the effluent water from the anaerobic fermentation step to be recycled into the process.

26 Claims, 4 Drawing Sheets

METHOD FOR PROCESSING LIGNOCELLULOSIC MATERIAL

FIELD OF THE INVENTION

Figure 1:
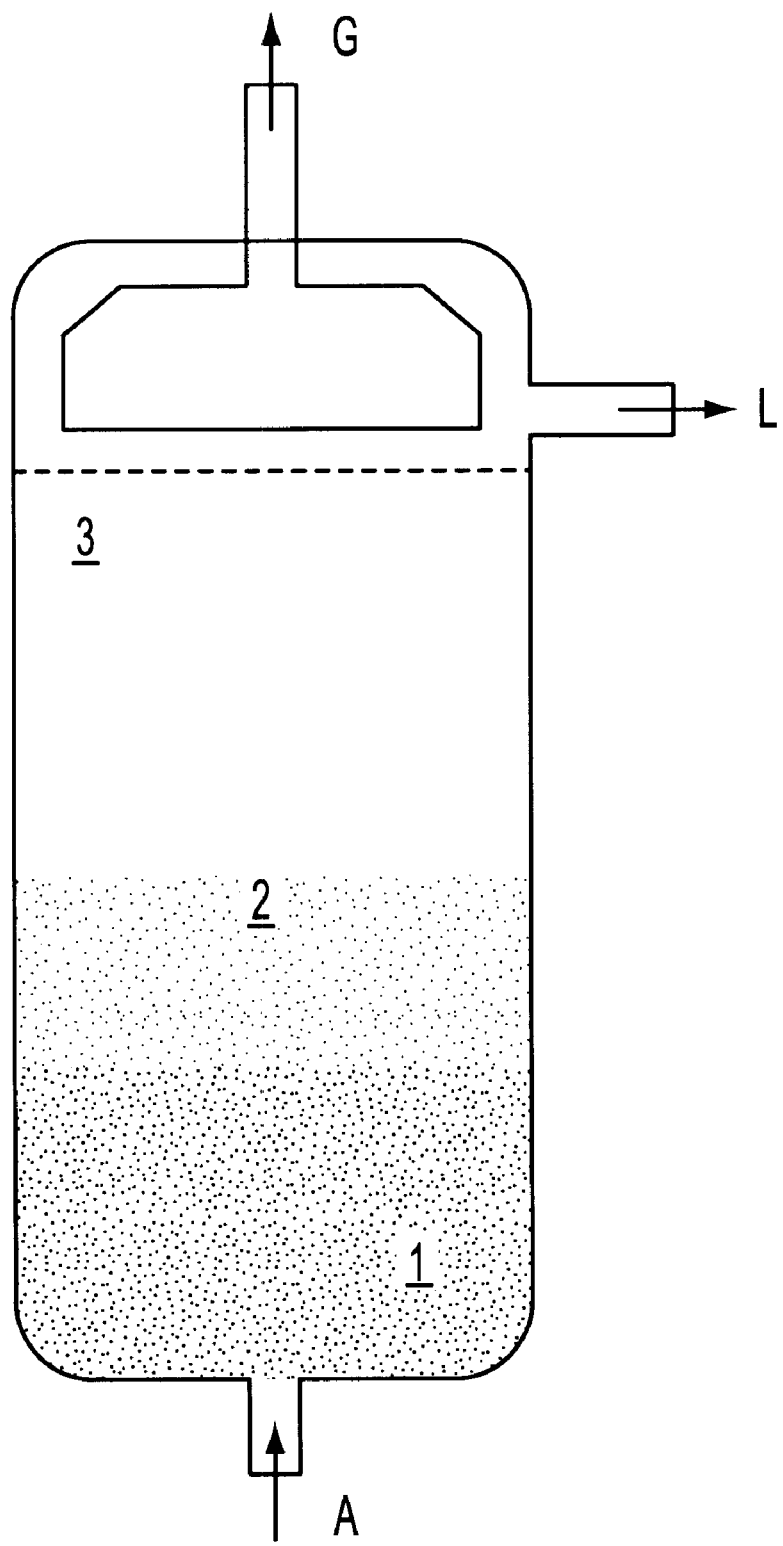

In its broadest aspect, the present invention relates to the conversion of lignocellulosic biomass materials into combustible fuel products. In particular, there is provided a continuous process for fermentatively converting such biomass materials into ethanol using a process design that permits all or part of the process water from the ethanol fermentation process to be recycled so as to significantly reduce the consumption of process water.

TECHNICAL BACKGROUND AND PRIOR ART

Increasing global energy requirements and heightened environmental awareness have resulted in increasing focus on alternatives to fossil fuels as energy sources. Human activity with respect to combustion of fossil fuels contributes significantly to the total amount of carbon dioxide ($CO_2$) released into the atmosphere. Carbon dioxide is purported to be a so called "greenhouse gas" and thus to contribute to global warming.

In contrast to energy production by combustion of fossil fuels, energy production by combustion of contemporary biomass (predominantly in the form of harvested plant material) or fuels derived from such biomass is regarded as being "$CO_2$-neutral", since the amount of $CO_2$ released by combustion of a given amount of such biomass corresponds to the amount of $CO_2$ which was originally taken up from the atmosphere during the build-up of that amount of biomass.

Among fuels derived from plant biomass, ethanol has received particular attention as a potential replacement for or supplement to petroleum-derived liquid hydrocarbon products. To minimise the production cost of ethanol produced from biomass (also referred to in the following as "bioethanol") It is important to use biomass in the form of low-cost by-products from gardening, agriculture, forestry, the timber industry and the like; thus, for example, materials such as straw, maize stems, forestry waste (log slash, bark, small branches, twigs and the like), sawdust and wood-chips are all materials which can be employed to produce bioethanol.

In general, however, the price of bioethanol has not been competitive with that of traditional fossil fuels and it is therefore highly needed to reduce production costs as far as possible by optimising or improving upon bioethanol production technologies.

One important factor in relation to bioethanol production on a commercial scale is the cost of the process water employed. In general, the aqueous effluent from conventional bioethanol production based on the above biomass materials contains substances at a level which, if such process water is recycled, will be rate limiting for the pre-treatment of the lignocellulosic material and/or inhibitory for subsequent hydrolysis of the pre-treated material and fermentation of sugars therein. Accordingly, it is a current practice in bioethanol production to dispose of this water effluent and replace it in the process with fresh process water.

There is thus an industrial need to design bioethanol production processes wherein all or part of the process water can be recycled.

In U.S. Pat. No. 5,221,357 there is described a process for treating a polysaccharide material such as cellulose, hemicellulose and lignocellulose by a two stage acidic hydrolysis to produce monosaccharides and a wet oxidation of the solids such as lignin to produce soluble products e.g. organic acids. The monosaccharides produced are subsequently subjected to fermentation to produce ethanol. Residues from wet oxidation and fermentation are subjected to a methanation step. However, in order to be capable of recycling the remaining liquid and solids into the system a secondary wet oxidation step after methanation is needed which is an additional cost in the production of ethanol.

Thus, the industry is not in the possession of any commercially attractive processes for continuously producing combustible fuel products which permit the process water to be recycled.

It is therefore one significant objective of the present invention to provide a process for continuously processing lignocellulosic material into valuable fuel products wherein the wastewater effluent from the ethanol fermentation effluent is subjected to a treatment, such as an anaerobic fermentation step generating a further combustible fuel product and a wastewater effluent in which the amount of potential inhibitory substances is at a sub-inhibitory level, which in turn permits all or part of the effluent water from the anaerobic fermentation step to be recycled into the process.

The process of the invention thus has the advantages of being capable of 1) giving a very high degree of conversion of carbon in the starting lignocellulosic biomass to useful products, 2) reducing the consumption of water used in the process, and 3) minimising the mounts of residual waste material emerging from the process.

Thus, the process of the invention not only provides improved process economy, e.g. with respect to production of a further combustible fuel product, but is also more environmentally friendly than traditional processes for obtaining such products.

SUMMARY OF THE INVENTION

Accordingly, the present invention pertains to a process for continuously converting solid lignocellulosic biomass material into ethanol, the method comprising the steps of:

(i) providing an aqueous slurry of the biomass material, (ii) subjecting, in a reaction vessel, said aqueous slurry to elevated temperature conditions and/or an oxygen enriched atmosphere to obtain a slurry in which at least partial separation of the biomass material into cellulose, hemicellulose and lignin has occurred, (iii) subjecting the slurry resulting from step (ii) and/or the aqueous phase hereof to a a treatment resulting in at least partial hydrolysis of the cellulose and hemicellulose to obtain a slurry and/or aqueous phase containing an amount of microbially fermentable sugars that permits the slurry or aqueous phase to be used as an ethanol fermentation medium, (iv) subjecting the slurry and/or aqueous phase of step (iii) to at least one ethanol fermentation step, (v) separating the ethanol from the fermentation medium resulting from step (iv) resulting in a fermentation wastewater effluent containing a level of inhibitory substances that, if present in any of the preceding steps (ii) to (iv) would be rate limiting or inhibitory;

(vi) subjecting said wastewater effluent to a treatment whereby the level of the inhibitory substances is reduced to a level that, if the wastewater effluent is introduced into any of the preceding steps (ii) to (iv) is not rate limiting or inhibitory;

(vii) introducing all or part of the thus treated wastewater effluent into any of the preceding steps (i) to (v), and (viii) continuously repeating steps (i) to (vii).

As shown herein, it was possible to provide a fully operational process for continuously converting solid lignocellulosic biomass material, which process comprises wet oxidation or treatment at an elevated temperature such as steam explosion, enzymatic hydrolysis, ethanol fermentation and finally wastewater treatment. An interesting feature of the process according to the invention is that it is not necessary to incorporate any detoxification steps in the process as all substances produced during each single step of the process served as a substrate for the organisms used in a subsequent step.

As described above, the lignocellulosic biomass material is subjected to a pre-treatment in step (ii), which is wet oxidation or a treatment at an elevated temperature such as e.g. steam explosion. If used, the amount of oxidising agent employed in this step will in general be an amount which is effective to substantially prevent or minimise formation of undesirable reduction products, e.g. furfural and/or furfural derivatives. A well suited oxidising agent is oxygen per se, and presently preferred processes of the invention are performed in the presence of oxygen introduced into the reactor at an initial partial pressure of oxygen equal to or exceeding ambient partial pressure of oxygen.

It appears that cellulose and any hemicellulose present in unsolubilized solid residue which may remain after performing a wet-oxidative or steam explosion treatment in step (ii) is rendered more susceptible relative to cellulose and hemicellulose in lignocellulosic material which has not been treated in the manner of the invention to chemical or enzymatic hydrolysis to give the constituent monosaccharides (D-glucose in the case of cellulose, and primarily D-xylose and/or other pentoses in the case of most hemicelluloses), hereby facilitating procedures such as fermentation to convert glucose or xylose to ethanol or to convert xylose to xylitol or lactose.

In relation to the above-mentioned application of enzymatic treatments or fermentation procedures, use of the process of the invention result in substantial removal of any microorganism- and/or enzyme-inhibitory substances such as acetate, 2-furfural and/or 5-hydroxymethyl-2-furfural, as well as phenolic substances such as vanillin, vanillic acid, homovanillic acid, acetosyringon, syringic acid, syringaldehyde, syringol and the like, which might otherwise accumulate in the process water as a consequence of the degradation of lignin and other substances in the first step of the process, and which may subsequently inhibit microorganisms and/or inhibit the catalytic action of enzymes added for the purpose of facilitating, for example, hydrolysis of cellulose to glucose or hydrolysis of components of solubilized hemicellulose, such as xylans, mannans or arabinans, to the corresponding monosaccharides.

DETAILED DISCLOSURE OF THE INVENTION

Accordingly, it has now been found that, in order to avoid, in the water used in the process, an accumulation of substances, such as carboxylic acid and other potential fermentation inhibitors produced during the disruption of the structure of lignocellulosic material by means of a pre-treatment such as wet-oxidation or steam explosion and during an ethanol fermentation step, it is possible to remove or at least reduce the amount of these substances to a sub-inhibitory level by applying an aerobic or anaerobic treatment step using one or more microorganisms which alone or together are capable of utilising the carboxylic acids and other fermentation inhibitors as nutrients, the level of which is thereby reduced.

In this manner it is possible to treat the wastewater effluent from the ethanol fermentation process to generate methane or other combustible biogases and a final treated wastewater, wherein the level of inhibitory substances that, if present in any of the steps of the process, i.e. during wet oxidation or steam explosion of the lignocellulosic biomass is performed in order to obtain at least partial separation of said biomass or when present during the subsequently hydrolysis or fermentation of sugars, would be rate limiting or inhibitory for said separation, hydrolysis and/or fermentation. Thus, in the present context, the expression "inhibitory substances" refers to substances such as carboxylic acids which inhibit the pre-treatment of the lignocellulosic biomass material and to substances, such as furans and phenols and carboxylic acids, which inhibit the ethanol fermentation. It appears that a very high percentage (often about 80% or more) of the organic matter, also referred to as chemical oxygen demand (COD) remaining after ethanol fermentation can be converted to biogas, thus minimising the amounts of waste materials emerging from the process.

As mentioned above, step (ii) of the process according to the present invention encompasses a wet oxidation or elevated temperature treatment, e.g. steam explosion of the lignocellulosic material. The terms "wet oxidation" and "wet-oxidative" as used herein refers to a process which takes place in an aqueous medium, i.e. liquid water or a liquid medium containing at least a substantial proportion of liquid water, in the presence of an oxidising agent which reacts oxidatively in some manner and to some extent with one or more components or species present (as a solid or solids, and/or in dissolved form) in the medium. The process normally takes place at an elevated temperature, i.e. at a temperature significantly above room temperature or normal ambient temperature (usually at a temperature of at least 100° C.), and at a pressure at least equal to the vapour pressure of water above the liquid aqueous medium at the temperature in question plus the partial pressure(s) of any other gas or gasses, e.g. oxygen, or (when using air) oxygen plus—primarily—nitrogen, present. The conditions (temperature, pressure) employed are such that the aqueous medium does not boil. The wet oxidation and the below discussed steam explosion convert a large portion of the biomass material to $CO_2$, $H_2O$ and simpler, more oxidised organic compounds, mainly low-molecular weight carboxylic acids.

As an alternative to wet oxidation the more well known steam explosion (Puls, 1993) or steaming can be successfully used in the process according to the invention. Steam explosion or steaming operate at the same temperature range of 170–220° C., e.g. a range of 180 to 210° C. and reaction time of 2–20 minutes, but the chemicals used differ and addition of water, prior to the treatment by soaking the biomass in weak acidic or alkaline solutions, is only optional. Steaming operates with saturated steam with or without prior addition of oxygen, carbon dioxide, sulphur dioxide or sulphuric acid as catalyst (Saddler et al, 1993).

As already indicated, processes according to the invention employ lignocellulosic material of plant origin, the lignocellulose, which is the principal component of such materials, in general being built up predominantly of cellulose, hemicellulose and lignin.

Cellulose, which is a β-glucan built up of anhydro D-glucose units, is the main structural component of plant cell walls and normally constitutes about 35–60% by weight (% w/w) of lignocellulosic materials.

Hemicellulose is the term used to denote non-cellulosic polysaccharides associated with cellulose in plant tissues. Hemicellulose frequently constitutes about 20–35% w/w of lignocellulosic materials, and the majority of hemicelluloses consists predominantly of polymers based on pentose (five-carbon) sugar units, such as D-xylose and D-arabinose units, although more minor proportions of hexose (six-carbon) sugar units, such as D-glucose and D-mannose units, are generally also present.

Lignin, which is a complex, cross-linked polymer based on variously substituted p-hydroxyphenylpropane units, generally constitutes about 10–30% w/w of lignocellulosic materials. It is believed that lignin functions as a physical barrier to the direct bioconversion (e.g. by fermenting microorganisms) of cellulose and hemicellulose in lignocellulosic materials which have not been subjected to some kind of pre-treatment process (which may very suitably be a wet-oxidative process as described in relation to the present invention) to disrupt the structure of lignocellulose.

To minimise the production cost of ethanol produced from biomass it is important to use biomass in the form of low-cost by-products from gardening such as garden refuse, waste materials from agriculture, forestry, the timber industry and the like. Thus, processes of the invention are applicable to any kind of hemicellulose-containing lignocellulosic materials. Relevant materials thus include wooden or non-wooden plant material in the form of stem, stalk, shrub, foliage, bark, root, shell, pod, nut, husk, fibre, vine, straw, hay, grass, bamboo or reed, singularly or in a mixture.

Preferred lignocellulosic materials in the context of the invention include wood (both softwood and hardwood), straw, corn stovers and so-called hulls. Wood employed in the context of the invention is generally heartwood (duramen) and/or outer wood (secondary xylem) derived from trunks, stems and/or branches of deciduous or evergreen trees or shrubs. Wood from the roots of such trees or shrubs may also be of value.

Useful sources of wood include numerous species of various genera of coniferous and broad-leaved trees/shrubs. Among conifers may be mentioned the following: Pinaceae, including pines (Pinus spp., such as *Pinus sylvestris*), silver firs (Abies spp., such as *Abies alba*), spruces (Picea spp., such as *Picea abies*), larches (Larix and Pseudolarix spp., such as *Larix decidua* and *L. kaempferi*) and Douglas fir (*Pseudotsuga menziesii*). Among broadleaves may be mentioned the following: Betulaceae, including birches (Betula spp., such as *Betula pendufa*); and Fagaceae, including beeches (Fagus spp., such as *Fagus sylvatica*) and oaks (Quercus spp., such as *Quercus robur*).

Useful sources of straw include in particular cereals (cereal grasses), i.e. gramineous plants which yield edible grain or seed. Straw from, for example, oat (Avena spp., such as *A. saliva*), barley (Hordeum spp., such as *H. vulgare*), wheat (Triticum spp., including *T. durum*), rye (*Secal cereale*), rice (Oryza spp.), millet (e.g. species of Digitaria, Panicum, Paspalum, Pennisetum or Setana), sorghum (Sorghum spp., including *S. bicolor* var. durra (also referred to as "durra") and milo), buckwheat (Fagopyrum spp., such as *F. esculentum*) and maize (also referred to as corn (*Zea mays*), including sweetcorn] is well suited for treatment according to the process of the invention.

As employed herein, the term "hull" generally denotes the outer covering, rind, shell, pod or husk of any fruit or seed, but the term as employed herein also embraces, for example, the outer covering of an ear of maize. Relevant hulls include hulls selected among the following:

hulls from oat (Avena spp., such as *A. saliva*), barley (Hordeum spp., such as *H. vulgare*), wheat (Triticum spp., including *T. durum*), rye (*Secal cereale*), rice (Oryza spp.), millet (e.g. species of Digiftaa, Panicum, Paspalum, Pennisetum or Setaria), sorghum (Sorghum spp., including *S. bicolor* var. durra and milo), buckwheat (Fagopyrum spp., such as *F. esculentum*), maize [also known as corn (*Zea mays*), including sweetcorn], corn cob, rape-seed (from Brassica spp., such as *B. napus, B. napus* subsp. rapifera or *B. napus* subsp. oleifera), cotton-seed (from Gossypium spp., such as *G. heraceum*), almond (*Prunus dulcis*, including both sweet and bitter almond) and sunflower seed (Helianthus spp., such as *H. annuus*).

Hulls of cereals, including not only those mentioned among the above, but also hulls of cereals other than those mentioned among the above, are generally of interest in the context of the invention, and preferred hulls, such as oat hulls and barley hulls, belong to this category. In this connection it may be mentioned by way of example that oat hulls are often available in large quantities at low cost as a by-product of oat-processing procedures for the production of oatmeal, porridge oats, rolled oats and the like; thus, a total of around 75,000 tons of oat hulls is produced per year as a by-product of oat-processing in Denmark, Norway and Sweden together with northern Germany.

Other types of hulls of relevance in relation to processes of the invention include, for example, palm shells, peanut shells, coconut shells, other types of nut shells, and coconut husk.

It should be noted that the native physical form, bulk and/or dimensions of lignocellulosic materials such as wood, straw, hay and the like will generally necessitate, or at least make it desirable, to carry out comminution of the material (e.g. by milling, abrading, grinding, crushing, chopping, chipping or the like) to some extent in order to obtain particles, pieces, fibres, strands, wafers, flakes or the like of material of sufficiently small size and/or sufficiently high surface area to mass ratio to enable degradation of the material to be performed satisfactorily. In the case of wood, material of suitable dimensions will often be available as a waste product in the form of sawdust, wood chips, wood flakes, twigs and the like from sawmills, forestry and other commercial sources.

In contrast, numerous types of hulls, e.g. cereal grain or seed hulls in general, including oat hulls as employed in the working examples reported herein, have in their native form sufficiently small dimensions and a sufficiently high surface area to mass ratio to enable them to be used directly, without prior comminution, as lignocellulosic materials in a process according to the present invention.

The initial ratio of solid lignocellulosic material to liquid aqueous medium in the wet-oxidation reactor will generally be in the range of 0.02–1 kg/liter, often 0.05–0.35 kg/liter, such as 0.05–0.2 kgl/liter, depending on the form, bulk and/or dimensions of the lignocellulosic material as treated. On an industrial scale it will normally be economically most advantageous to perform the process of the invention at the highest practicable ratio of lignocellulosic material to liquid, aqueous medium, i.e. at the highest ratio which permits adequate mixing of the lignocellulosic material in the liquid medium comprising the oxidising agent and which leads to a satisfactorily high rate of degradation of lignocellulose.

By using certain materials of types preferred in the context of the present invention and in the manner disclosed herein it is thus possible, on an industrial scale, to avoid having to use time- and energy-consuming—and thereby expensive—comminution procedures which require investment in, and maintenance of, appropriate comminution apparatus or machinery.

Further to the above, it may nevertheless be desirable with certain types of lignocellulosic materials (e.g. shells of certain nuts) among those of relevance in relation to the present invention to subject the material in question, before treatment by a process of the invention, to a comminution procedure (e.g. by milling, abrading, grinding, crushing, chopping, chipping or the like) in order to enhance the overall reactivity of the material by enhancing, e.g., the physical mobility, mixability, ratio of surface area to mass and the like of the material.

Pre-Treatment of Lignocellulosic Material (Steps (i) and (ii) of the Process According to the Invention)

As described above, the first step in the process for continuously converting solid lignocellulosic biomass material into ethanol, is to provide an aqueous slurry of the lignocellulosic biomass material. The thus obtained slurry is in step (ii) of the process subjected to elevated temperature conditions and/or an oxygen enriched atmosphere to obtain a slurry in which at least partial separation of the biomass material into cellulose, hemicellulose and lignin has occurred.

In one preferred embodiment, the aqueous slurry in step (ii) is subjected to a wet of the oxidation treatment discussed in detail above. In another useful embodiment of the present process, the aqueous slurry in step (ii) is subjected to a steam explosion treatment as also discussed above. In the present context the wet oxidation treatment and the steam explosion treatment of the lignocellulosic biomass material is referred to as pre-treatment. It will be understood that the steam explosion treatment optionally can be performed without providing the lignocellulosic biomass material as an aqueous slurry.

Oxidising Agents

As already indicated, if an oxidising agent is present during the pre-treatment, a preferred oxidising agent in the context of processes according to the invention is oxygen per se.

Other oxidising agents which may—at suitable concentrations and under suitable conditions of temperature and reaction time—be appropriate for use in a wet-oxidative process in the manner of the invention include, in particular, hydrogen peroxide. Hydrogen peroxide is very soluble in water, is readily available commercially as aqueous solutions of concentration ranging from relatively dilute (e.g. hydrogen peroxide concentrations of around 3% w/w) to relatively concentrated (e.g. hydrogen peroxide concentrations of about 30–35% w/w) and is—like oxygen—a very acceptable oxidising agent from an environmental point of view.

Hydrogen peroxide is thus generally well suited for inclusion—either alone or in combination with one or more other oxidising agents, e.g. oxygen—as an oxidising agent in the liquid, aqueous medium employed, and in such cases the initial concentration of hydrogen peroxide in the liquid, aqueous medium will normally suitably be in the range of 0.5–10% w/w.

Oxidising substances which are not well suited as oxidising agents in the context of the process of the invention include oxidising acids, such as concentrated or dilute nitric acid.

When oxygen is employed as oxidising agent, it is preferred—as mentioned previously—that the process is performed in the presence of oxygen introduced at an initial partial pressure of oxygen equal to or exceeding the ambient partial pressure of oxygen (i.e. the partial pressure of oxygen in the surrounding air, which at sea level is normally around 0.2 bar, typically about 0.21 bar), and initial oxygen partial pressures which lie in the range from about 0.2 to about 35 bar will normally be of interest. It is, however, generally prefer-able to employ initial oxygen partial pressures of at least 0.5 bar, normally in the range of 0.5–35 bar. Typical initial partial pressures of oxygen will be in the range of 1–15 bar, such as 3–12 bar, e.g. 5–12 bar. The solubility of oxygen in water at temperatures of relevance for the process of the invention increases with oxygen partial pressure, and the use of such elevated partial pressures of oxygen can thus be advantageous in ensuring the availability of sufficient oxygen in dissolved form.

The oxygen employed may be added in the form of substantially pure oxygen or in the form of an oxygen-containing gas mixture (such as atmospheric air) which in addition to oxygen is constituted by one or more other gases (e.g. nitrogen and/or an inert gas, such as argon) that are not detrimental to the performance of the process of the invention; it will, however, often be advantageous to employ substantially pure oxygen (such as oxygen of $\geq 99\%$ purity, which is readily commercially available in conventional gas cylinders under pressure).

When employing oxygen as oxidising agent, an appropriate, effective quantity of oxygen (or oxygen-containing gas mixture) may—particularly in the case of batch processes in which a chosen quantity (batch) of appropriate lignocellulosic material is treated according to the invention in a reactor which may be closed and, optionally, pressurised—be introduced into the reactor in question as a single charge at an appropriate initial pressure. Reactors of this type employed in batch processes for wet-oxidative treatment in the manner of the invention will, in addition to containing a certain volume of aqueous liquid phase in which the solid lignocellulosic material in question is contained, generally enclose a free volume or headspace above the liquid phase, and disregarding other considerations it will then be apparent that the greater the ratio of the headspace volume to the liquid phase volume, the lower the initial pressure (partial pressure) of oxygen that will be required to ensure the presence of an effective amount of oxygen gas within the reactor; the partial pressure of oxygen in the reactor—measured at the initial temperature in the reactor or reaction vessel—will decrease during the course of the process of the invention owing to consumption of oxygen in the oxidation reactions which occur.

By way of example only, when a batch reactor which can be closed and pressurised (e.g. a loop-reactor of the type described herein) is operated with an aqueous liquid phase containing about 60 grams of lignocellulosic material per liter of liquid phase, an appropriate effective amount of oxygen will typically be ensured by employing a ratio of headspace volume to liquid phase volume of about 1:1 and an initial oxygen pressure (partial pressure) in the range of 0.2–12 bar. Moreover, since the solubility of oxygen (and a number of other gases, including nitrogen) in water at partial oxygen pressures of interest in the present context increases with temperature above about 100° C., and increases rapidly with temperature above about 140° C., it will generally be advantageous—not only with such closed batch reactors, but also with other types of reactors—to employ temperatures in excess of this latter temperature in order to ensure the presence of an adequate concentration of dissolved oxygen; for the same reason it will be possible by increasing the temperature further to employ relatively lower partial pressures of oxygen and still achieve satisfactory concentrations of dissolved oxygen in the liquid, aqueous medium.

As an alternative (which will almost always be employed in the case of continuous or substantially continuous processes, i.e. processes in which lignocellulosic material enters the wet-oxidation reactor essentially continuously, and products of the process exit or are withdrawn from the reactor essentially continuously), oxygen or an oxygen-containing gas mixture may be introduced essentially continuously (or at least at suitably frequent intervals) into the reactor at a suitable pressure so as to ensure the continued availability of sufficient oxidising agent.

Reaction Vessel

Reaction vessels useful to perform the wet-oxidative treatment or steam explosion in step (ii) of the process according to the present invention are usually containers and the like which are generally closed (not open to the surrounding atmosphere) and, optionally, pressurizable reaction vessels; some types of closed, pressurizable reaction vessels suitable for, in particular, batch-type wet-oxidative treatment in the manner of the invention have already been mentioned above. In one embodiment of the present invention, step (ii) is performed as a batch process in a closed, pressurizable reaction vessel having a free volume for containing oxygen-containing gas and/or water vapour.

Relevant types of reaction vessels for performing batch or essentially continuous processes such as wet oxidation or steam explosion include substantially vertically disposed reaction vessels in which the liquid, aqueous medium and the lignocellulosic material in question may be contained and into which oxygen or an oxygen-containing gas mixture (suitably air) may be introduced—continuously or at intervals—under pressure via one or more inlets, ports, valves or the like situated at or near the bottom of, and for at other locations along the length of, the reaction vessel containing the aqueous slurry of the lignocellulosic material; such reactors, which may suitably, but optionally, have an upper headspace or free volume, may be essentially cylindrical, tubular or of any other appropriate form. Vertical tower reaction vessels suitable for use in the context of the invention are described, for example, in GS 706,686 and GB 812,832.

Reaction vessels for performing continuous or essentially continuous wet-oxidative treatment or treatment at elevated temperatures using e.g. steam explosion in the manner of the invention may, for example, also be tubular or substantially tubular reaction vessels—very suitably essentially horizontally disposed—through which the liquid phase is pumped or otherwise driven, and which in principle have little or no headspace (free volume) available for, e.g., oxygen in gaseous form. Such reaction vessels will normally comprise one or more appropriately positioned injection inlets, ports, valves or the like for admitting oxygen gas (or, less preferably, an oxygen containing gas mixture) or steam under pressure more or less directly into the liquid phase—e.g. near the beginning of the reaction vessel (reckoned in the direction of flow of liquid within the reaction vessel) and optionally at one or more further positions along the length of the reaction vessel—such that at least a substantial proportion of the introduced oxygen or heated water vapour dissolves in the liquid medium, thereby bringing it into intimate contact with lignocellulosic material in question and thus maximising the oxidising efficiency of the introduced oxygen or the degradation effect of the heated water vapour.

In both batch and continuous wet-oxidative or elevated temperature processes according to the invention, it is generally desirable, where possible, to cause mixing of the aqueous slurry and any gas phase per se which may be present in the reaction vessel. This may suitably be achieved by mechanical stirring of the slurry, although agitation of the reaction vessel as a whole or other means of causing mixing may be applicable. In the case of batch processes employing a recirculatory reaction vessel of the general type as described below (the "loop-reactor" in which the liquid phase is recirculated via a tubular section of the reaction vessel by means of a pump, impeller wheel or the like, adequate mixing is generally ensured by the recirculation of the liquid phase (containing lignocellulosic material) at a suitable rate. Thus, one preferred embodiment of the present invention, is where step (ii) is performed as a batch process in a closed, pressurizable reaction vessel with recirculation of the reaction mixture. Similarly, when performing an essentially continuous process in a reaction vessel which is substantially tubular, cylindrical or the like, adequate mixing will often be achieved by causing a sufficiently high rate of flow of liquid phase (containing lignocellulosic material) through the tube(s), cylinder(s) or the like of the reaction vessel.

Temperature

As already mentioned, preferred conditions in step (ii) of the present process include the use of temperatures in the vicinity of, or in excess of, 100° C. In general, temperatures in the range of 120–240° C., such as 180–220° C., more typically in the range of 180–210° C., will be appropriate for the vast majority of such embodiments of the process according to the invention, and when using lignocellulosic materials of preferred types it will be usual to employ temperatures in the range of 160–210° C., such as 180–210° C. Good results appear to be obtainable with temperatures around 185–195° C. or 170–190° C. As already indicated, the temperature employed should be a temperature at which boiling of the liquid, aqueous medium does not occur under the pressure conditions in question. However, in preferred embodiments, the temperature in which step (ii) is performed is less than 220° C., such as less than 200° C., e.g. less than 195° C. including less than 190° C., e.g. less than 185° C., such as less than 180° C. including less than 175° C.

It is, however, desired to set the temperature so as to obtain the desired separation of the lignocellulosic biomass material into cellulose, hemicellulose and lignin, without the destruction of to many polysaccharide molecules, as these molecules serve as a direct nutrient for the ethanol producing organisms in the subsequent step of the present process. As shown in the below Examples, e.g. in Table 2.2, there is a correlation between the reaction time and the temperature used in the reaction vessel. In general it is has been shown that the shorter the reaction time applied the higher temperature is needed in order to obtain a satisfactory separation of the lignocellulosic biomass material.

Heat may be supplied to the reaction mixture (notably the liquid phase/lignocellulosic material) by any suitable method, such as by immersing the reaction vessel in an appropriate heating bath (comprising, e.g., an oil, a molten salt or molten salt mixture, super-heated steam, etc.), by means of thermally conductive (typically metal) tubing which is wound around the outside of the reaction vessel, and for is immersed in the reaction medium itself, and through which suitably hot oil, superheated steam or the like is passed, or—similarly—by means of one or more electrical resistance heating elements wound around the outside of the reaction vessel and/or immersed in the reaction medium. Other applicable methods of heating include induction heating (e.g. of a metal reaction vessel casing) and microwave heating.

It should be noted here that the degradation reactions taking place in the wet-oxidative treatment or steam explosion treatment which is a preferred feature of the process of the invention normally lead to oxidation or heat effected degradation of a certain proportion of the organic material, notably lignin and some hemicellulose, but also in many cases pectin (which is often present to some extent in lignocellulosic materials), in the lignocellulosic material employed. These oxidative or heat generated reactions are beneficial in the sense that they are, in general, exothermic, and the heat generated thereby contributes to reduce the quantity of thermal energy which has to be supplied to the reaction mixture in the reaction vessel in order to maintain the desired temperature.

Reaction Time

Heating of the lignocellulosic material(s) in the liquid, aqueous medium in a wet-oxidative treatment or by steam explosion in the manner according to the invention will normally be carried out for a period of time ranging from about 1 minute to about 1 hour (i.e. about 1–60 minutes), depending not only on the other reaction conditions (e.g. the reaction temperature, and the type and concentration of oxidising agent) employed, but also on the reactivity (rate of reaction) of the lignocellulosic material. In practicable embodiments of the process of the invention, step (ii) will normally employ reaction times in the range of 5–30 minutes, often 5–15 minutes, and when other reaction conditions are in preferred ranges, such as an oxygen (partial) pressure in the range of about 3–12 bar, e.g. 3–10 bar, and a temperature in the range of about 160–210° C., suitable reaction times will often be in the range of about 10 to about 15 minutes.

Adjustment of pH in the Reaction Mixture

In many cases, the treatment performed in step (ii) may be carried out with satisfactory results without any adjustment of the pH, i.e. neutral, of the aqueous slurry before, or during, the performance of the treatment. However, for some types of lignocellulosic materials of relevance in the context of the invention it may be advantageous to adjust the pH of the reaction mixture before and/or during performance of the treatment. The pH may be decreased, i.e. acidic conditions, but in general the pH of the reaction mixture is increased (i.e. alkaline) by adding appropriate amounts of an alkali or base (e.g. an alkali metal hydroxide such as sodium or potassium hydroxide, an alkaline earth metal hydroxide such as calcium hydroxide, an alkali metal carbonate such as sodium or potassium carbonate or another base such as ammonia) and/or a buffer system. Thus, in an interesting embodiment of the present invention the aqueous slurry is subjected to alkaline conditions in step (ii).

As mentioned above, a major objective of the treatment in step (ii) is to break down the lignocellulosic material into hemicellulose and cellulose. Because the dissolved polysaccharides, i.e. cellulose and hemicellulose, and the sugars and carboxylic acids produced during the pre-treatment serve as a direct nutrient source for the microorganisms used in the subsequent ethanol and methane fermentations, respectively, a gentle break down is desired, i.e. the destruction of the polysaccharides is not desired. Thus, an important embodiment of the present process, is wherein at least 60% of the polysaccharide contained in the solid lignocellulosic biomass material is recovered in the slurry and/or aqueous phase after the aqueous slurry has been subjected to a pre-treatment in step (ii), such as at least 60%, e.g. at least 70% including at least 80%, such as at least 90% of the polysaccharides are recovered.

It has been shown that the unsolubilized solid residue remaining after performing step (ii) of the process of the invention appears is well suited for use as animal feed, or as a supplement to animal feed, for animals—notably ruminants, such as cattle, sheep, goats or deer—of importance in farming or agriculture. The solid residue remaining at this stage, which is generally rich in cellulose fibres, also appears to have applications in the areas of plant-growth media (e.g. in potting soils/composts and in organic media of the peat moss type and the like), soil-improvement agents (materials added to soil to improve, e.g., water retention, soil aeration, root penetration, etc.) and composite materials [structural materials which are produced by combining the solid residue with one or more other materials (e.g. a plastic such as polyethylene or polypropylene) in appropriate ratios, and which have modified properties relative to those of the latter material(s)].

Hydrolysis of the Slurry and/or Aqueous Phase (Step iii of the Process According to the Invention)

Subsequently to the treatment of step (ii) the slurry and/or the aqueous phase hereof is subjected to a treatment resulting in at least partial hydrolysis of the cellulose and hemicellulose to obtain a slurry and/or aqueous phase containing an amount of microbially fermentable sugars that permits the slurry or aqueous phase to be used as an ethanol fermentation medium.

The purpose of such a hydrolysis treatment is to hydrolyse oligosaccharide and possibly polysaccharide species produced during the wet oxidative treatment or steam explosion in step (ii) of cellulose and/or hemicellulose origin to form fermentable sugars (e.g. glucose, xylose and possibly other monosaccharides). Such treatments may be either chemical or enzymatic. However, in accordance with the invention the cellulose may instead of being converted to glucose be used as fibres in the paper industry.

Chemical hydrolysis may normally very suitably be achieved in a known manner by treatment with an acid, such as treatment with dilute (e.g. 2–10% w/w, typically 4–7% w/w) aqueous sulphuric acid, at a temperature in the range of about 100–150° C., e.g. around 120° C., for a period of 5–15 minutes, such as 5–10 minutes. Treatment with ca. 4% w/w sulphuric acid for 5–10 minutes at ca. 120° C. is often very suitable.

Enzymatic hydrolysis may likewise be achieved in a known manner by treatment with one or more appropriate carbohydrase enzymes (glycosidases, EC 3.2). In preferred embodiments, the carbohydrase enzyme is selected from the group consisting of a cellulase (EC 3.2.1.4) in the case of hydrolysis of cellulose or cellulose fragments; a xylanase (such as an endo-1, 4-β-xylanase, EC 3.2.1.8) in the case of hydrolysis of xylans; a β-glucanase including a glucan-1, 3-βglucosidase (exo-1, 3-β glucanase, EC 3.2.1.58) or an endo-1, 3(4)-β-lucanase, EC 3.2.1.6, in the case of hydrolysis of soluble fragments of cellulose to glucose, a pectinase (polygalacturonase, EC 3.2.1.15) in the case of hydrolysis of pectate and other galacturonans. Commercial enzyme products of relevance in this connection include Celluclast™, available from Novo Nordisk A/S, Bagsvaerd, Denmark, e.g. as Celluclast™ 1.5 L (a liquid preparation). Celluclast exhibits both cellulase activity (degrading cellulose to glucose, cellobiose and higher glucose polymers) and some degree of xylanase activity.

Fermentable sugars, notably monosaccharide product(s), obtained by hydrolysis are useful for further transformation to give other useful products (e.g. ethanol or xylitol). Thus, glucose (derived from cellulose) and xylose (derived from xylans in hemicellulose) may be transformed to ethanol using relevant fermenting microorganisms as described herein, and xylose may, for example, alternatively be transformed to xylitol by established methods (e.g. by catalytic hydrogenation or by fermentation).

Preferred embodiments, include those where the slurry and/or aqueous phase obtained in step (iii) contains, calculated on the total carbohydrate content, at least 40% microbially fermentable sugars, such as at least 50% fermentable sugars, e.g. at least 60% fermentable sugars including at least 70% fermentable sugars.

Ethanol Fermentation (Step iv of the Process According to the Invention)

In a further step of the process according to the invention the slurry and/or aqueous phase of step (iii) is subjected to at least one fermentation step employing one or more fermenting microorganisms capable of degrading oligo- and/or monosaccharides present in said liquid phase to form ethanol.

It will be understood, that it is possible, if desired, to combine process step (iii) and (iv) in the same reaction vessel, and thus performing hydrolysis to microbial fermentable sugars and simultaneously ferment these to ethanol utilising one or more microorganisms.

With regard to fermentation of, e.g., glucose to yield ethanol, any microorganism capable of converting glucose to ethanol can be used in the process according to the invention. For example, a suitable microorganism include a mesophilic microorganism (i.e. one which grows optimally at a temperature in the range of 20–40° C.), e.g. a yeast also referred to as "baker's yeast", *Saccharomyces cerevisiae*.

With regard to fermentation of, e.g. xylose to yield ethanol, any microorganism capable of converting xylose to ethanol can be used in the process according to the invention. Useful microorganisms include e.g. certain types of thermophiles (i.e. organisms which grow optimally at an elevated temperature—normally a temperature in excess of about 50° C.) and genetically engineered microorganisms derived therefrom. In preferred embodiments, a suitable organism for the ethanol fermentation is selected from the group consisting of Thermoanaerobacter species including *T. mathranii*, Zymomonas species including *Z. mobilis* and yeast species such as *Pichia species*. An example of a useful strain of *T. mathranii* is described in Sonne-Hansen et al., 1993 or Ahring et al. 1996 where said strain is designated as strain A3M4.

It will be appreciated, that a useful ethanol-fermenting organism can be selected from a genetically modified organism of one of the above useful organisms having, relative to the organism from which it is derived, an increased or improved ethanol-fermenting activity. As used herein the expression "genetically modified bacterium" is used in the conventional meaning of that term i.e. it refers to strains obtained by subjecting a organism to any conventionally used mutagenization treatment including treatment with a chemical mutagen such as ethanemethane sulphonate (EMS) or N-methyl-N'-nitro-N-nitroguanidine (NTG), UV light or to spontaneously occurring mutants, including classical mutagenesis. Furthermore, as it is possible to provide the genetically modified bacterium by random mutagenesis or by selection of spontaneously occurring mutants, i.e. without the use of recombinant DNA-technology, it is envisaged that mutants of the above mentioned organism can be provided by such technology including site-directed mutagenesis and PCR techniques and other in vitro or in vivo modifications of specific DNA sequences once such sequences have been identified and isolated.

Using microorganisms with different optimal growth temperature requirements to ferment glucose and xylose, respectively, to yield ethanol, it may thus be desirable to perform the fermentation step in question as a two-stage process wherein the slurry and/or aqueous phase after the preceding step (iii) is first contacted with one of the microorganisms under appropriate conditions therefore (e.g. *S. cerevisiae* at a temperature of around 30° C.) and subsequently with the other microorganism under its appropriate conditions (e.g. *T. mathranii* at a temperature of about 70° C.). The two stages may suitably take place in separate fermentation reaction vessels or in the same reaction vessel in a sequential manner.

Fermentation reaction vessels (fermentors) of any suitable, known type may be employed in performing one or more fermentation steps of the type in question. For further details of suitable reaction vessels, reference may be made, for example, to J. E. Bailey and D. F. Ollis, 1986. Batch fermentation and continuous fermentation are both suited in this connection.

Subsequent to the ethanol fermentation step, the ethanol is separated from the fermentation medium resulting from step (iv) resulting in a fermentation wastewater effluent containing a level of inhibitory substances that, if present in any of the preceding steps (ii) to (iv) would be rate limiting for the at least partial separation of the biomass material and/or he liberation of sugars and ethanol fermentation. As used herein, the expression "inhibitory substances that, if present in any of the preceding steps (ii) to (iv) would be rate limiting for the at least partial separation of the biomass material and/or the liberation of sugars and ethanol fermentation" relates to substances produced during the wet oxidation or steam explosion performed in step (ii) and by the ethanol fermenting organisms used in step (iv). Such substances include carboxylic acids such as acetic acid and lactic acid, and furans including 5-hydroxymethylfurfural, 2-furfural and 2-furoic acid and phenols including guaiacol, syringol, 4-hydroxy benzalde-hyde, vanillin, syringaldehyde, 3,4,5-tri-methoxybenzaldehyde, 4-hydroxy aceto-phenone, acetovanillone, acetosyringone, 3,4,5-trimethoxyacetophenone, 4-hydroxy benzoic acid, vanillic acid, syringic acid, p-coumaric acid and ferulic acid.

In addition, the expression "rate limiting level" is used in the present context, to indicate a concentration of the above inhibitory substances which inhibits or reduces the performance of the pre-treatment, hydrolysis and/or ethanol fermentation. If the wet oxidation or steam explosion is performed under conditions of increasing concentrations of organic acids, such as carboxylic acids, i.e. when the water used is process water recycled from the process contains a high concentrations of organic acids, the fractionation of the cellulose and hemicellulose is compromised. In addition, more carboxylic acids and furans are produced under the pre-treatment which in a potential concentration inhibits microbial growth.

Treatment of the Wastewater Effluent (Step vi of the Process According to the Invention)

As already indicated, the process according to the invention comprises subsequently subjecting the wastewater effluent obtained in steps (v) and (vi) to a treatment, such as a biological treatment, whereby the level of the inhibitory substances is reduced to a level that, if the wastewater effluent is introduced into any of the preceding steps (ii) to (iv), is not rate limiting for the pre-treatment or inhibiting the hydrolysis and/or ethanol fermentation process.

In a preferred embodiment, such treatment is an anaerobic fermentation process employing one or more anaerobic fermenting microorganisms capable of degrading of converting substances present in said wastewater effluent to form combustible fuel such as methane.

Microorganisms

In one useful embodiment of the present invention, the treatment in step (vi) is performed using methane-producing microorganisms (also known as methanogens) which constitute a unique group of prokaryotes which are capable of forming methane from certain classes of organic substrates, methyl substrates (methanol, methylamine, dimethylamine, trimethylamine, methylmercaptan and dimethylsulfide) or acetate (sometimes termed acetoclastic substrate) under anaerobic conditions.

Methanogens are found within various genera of bacteria, and methanogenic bacteria of relevance in the context of the present invention include species of Methanobacterium, Methanobrevibacter, Methanothermus, Methanococcus, Methanomicrobium, Methane genium, Methanospirillum, Methanoplanus, Methanosphaera, Methanosarcina, Methanolobus, Methanoculleus, Methanothrix, Methanosaeta, Methanopyrus or Methanocorpusculum; some of these, notably species of Methanopyrus, are highly thermophilic and can grow at temperatures in excess of 100° C. Only three genera of methanogenic bacteria, viz. Methanosarcina, Methanosaeta and Methanothrix, appear to contain species capable of carrying out the acetoclastic reaction, i.e. conversion of acetate to methane (and carbon dioxide). It will be appreciated that useful methanogenic bacteria can be selected from a genetically modified bacterium of one of the above useful organism having, relative to the organism from which it is derived, an increased or improved methane producing activity. Such a genetically modified organism can be obtained by the methods discussed above.

In the context of the present invention it will generally be most appropriate to apply, in addition to one or more methanogens, other types of microorganisms which, alone or in combination, are capable of degrading organic substances present in the material to be treated in the anaerobic fermentation step of the process of the invention, but which are not directly suited as substrates for the methanogen(s) employed in the anaerobic fermentation step. Such other types of microorganisms include certain fermentative anaerobic bacteria capable of converting, for example, glucose to products such as acetate, propionate, butyrate, hydrogen and $CO_2$, and so-called acetogenic bacteria, which convert organic substances such as propionate, butyrate and ethanol to acetate, formate, hydrogen and $CO_2$.

However, the treatment of the wastewater effluent may also be performed as an aerobic treatment, used aerobic organisms capable of utilising the above mentioned inhibitory substances so as to reduce such substances to a level that, if the wastewater effluent is introduced into the reaction vessel of step (ii) or in any other step of the process, is not rate limiting.

Reaction Vessel Types

The treatment process in step (vi) of the process of the invention is suitably carried out using a reaction vessel of a type known as an "Upflow Anaerobic Sludge Blanket" reactor (UASB reactor) as for example described in Schmidt and Ahring (1996). A schematic drawing of a reactor of this type, which normally has the general form of a substantially vertically oriented cylinder, is shown in FIG. 1.

Recycling of the Treated Wastewater Effluent (Steps vii and viii of the Process According to the Invention)

As already indicated above, it is a very important feature of the invention that all or part of the thus treated wastewater effluent remaining after completing the treatment in step (vi) is recycled for reuse as aqueous liquid phase in the process of the invention thereby reducing the consumption of water and minimising the quantity of waste material emerging from the process. By using the treated wastewater effluent for any step of the process according to the invention, i.e. for obtaining the aqueous slurry in step (i) and/or by introducing the treated wastewater effluent into the reaction vessel of step (ii) and/or into the reaction vessel of steps (iii) to (iv), it is possible to continuously repeating steps (i) to (vii), and thus continuously converting solid lignocellulosic material into ethanol and methane.

Accordingly, in preferred embodiments, at least 5% of the wastewater effluent resulting from step (v) is introduced into any step of the process according to the invention, such as at least 10% e.g. at least 20% including at least 30%, such as at least 40% e.g. at least 50% including at least 60% such as at least 70% e.g. at least 80% including at least 90% or even 100%. The introduction of the treated wastewater into the preceding process steps can occur substantially without decreasing the production of ethanol or methane in said steps.

Thus, the purpose of the wastewater treatment in step (vi) of the present process is to reduce the organic matter (COD), i.e. the inhibitory substances, such as carboxylic acids, furans and phenolic compounds, present in the wastewater, in order, when the treated wastewater effluent is reintroduced into the process, to secure that the concentration of inhibitory substances is not at a rate limiting or inhibitory level for the partial separation of the biomass material and/or to the hydrolysis and/or ethanol fermentation. Accordingly, a very high percentage of the organic matter (COD) remaining after ethanol fermentation is converted to biogas. Thus, in preferred embodiments, at least 50% COD remaining after the ethanol fermentation is converted to biogas, such as at least 60%, e.g. at least 70% including at least 80%, such as at least 85%. As shown in the below examples, it is possible by performing step (vi) to reduce the level of the inhibitory substances in the fermentation wastewater effluent present in step (vi) by at least 80%, such as at least 85%, e.g. at the least 90% including at least 95% or even by 100%.

Figure 2:
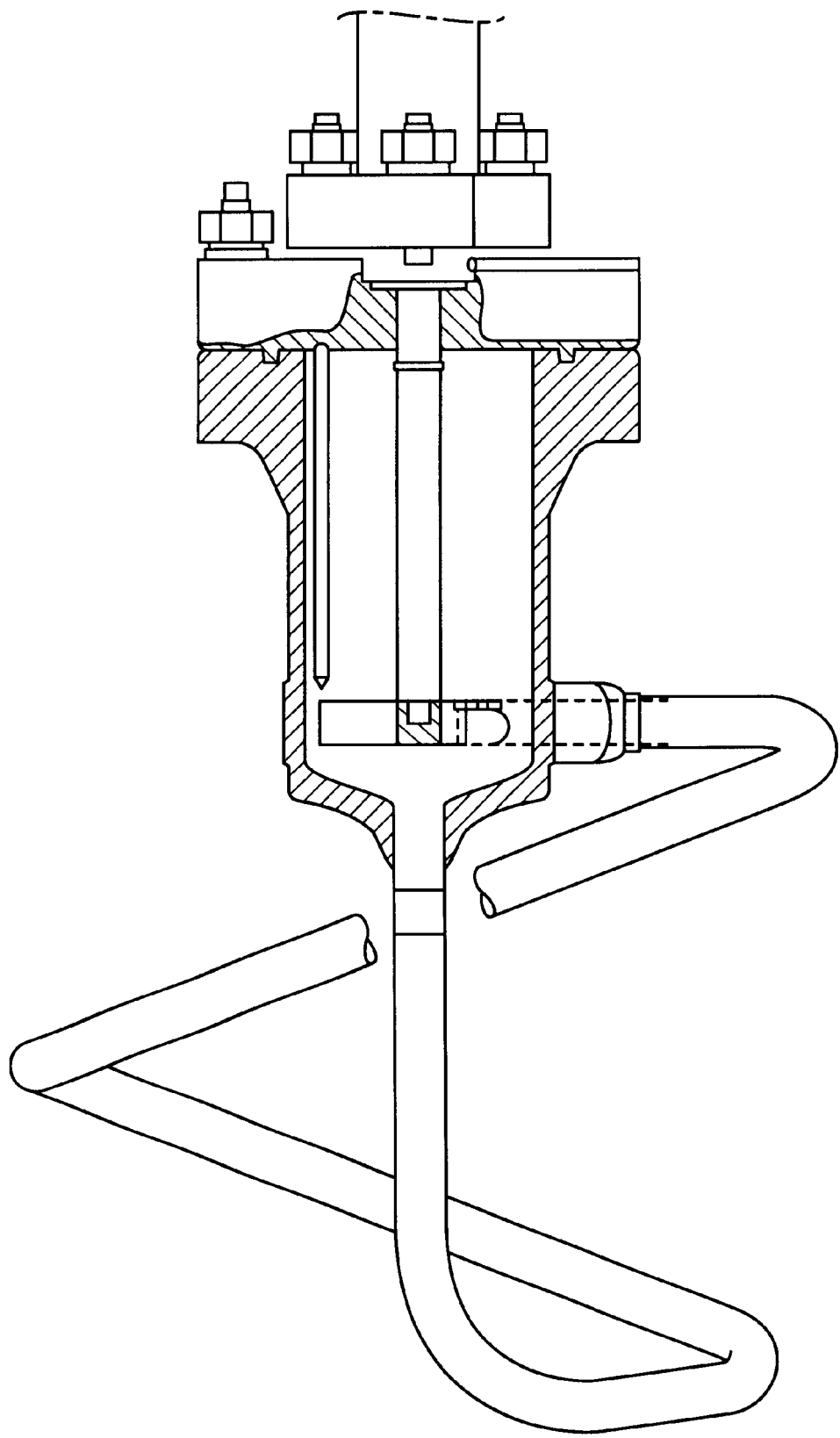
Figure 3:
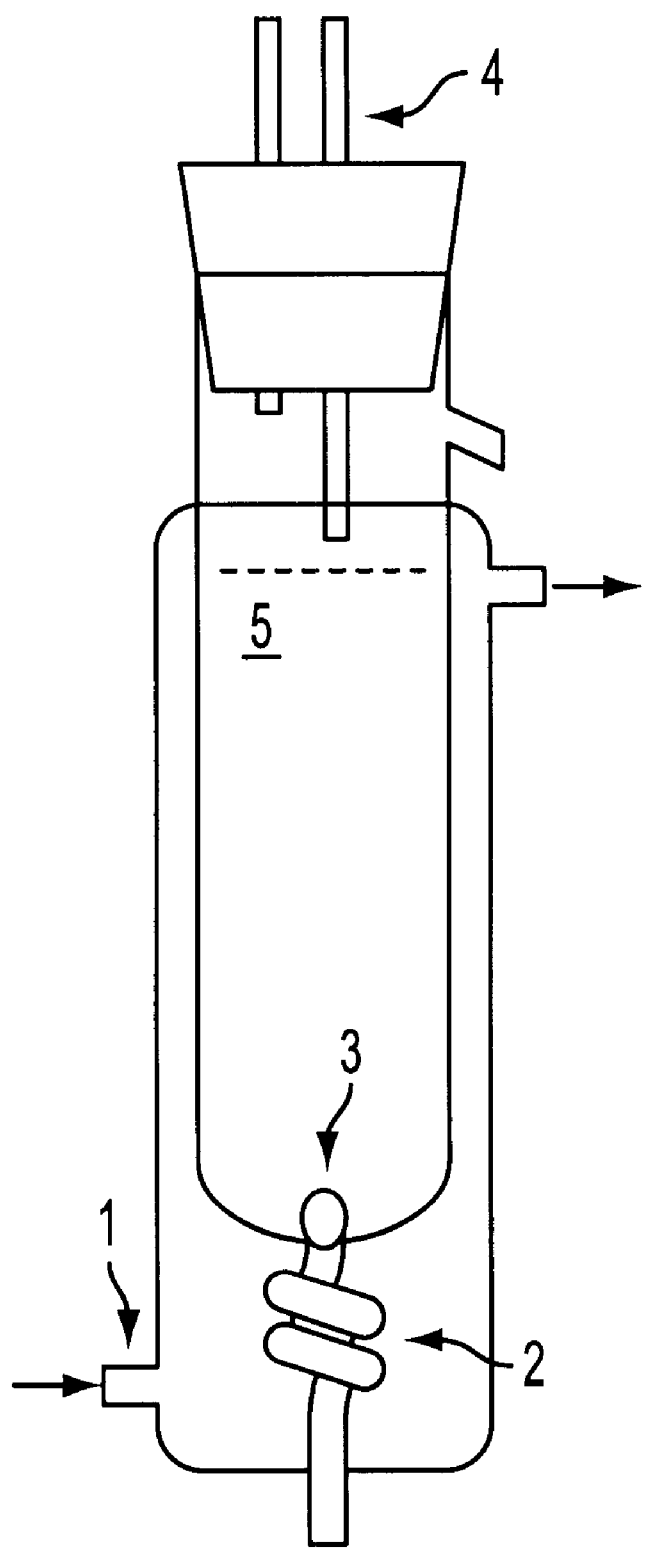
Figure 4:
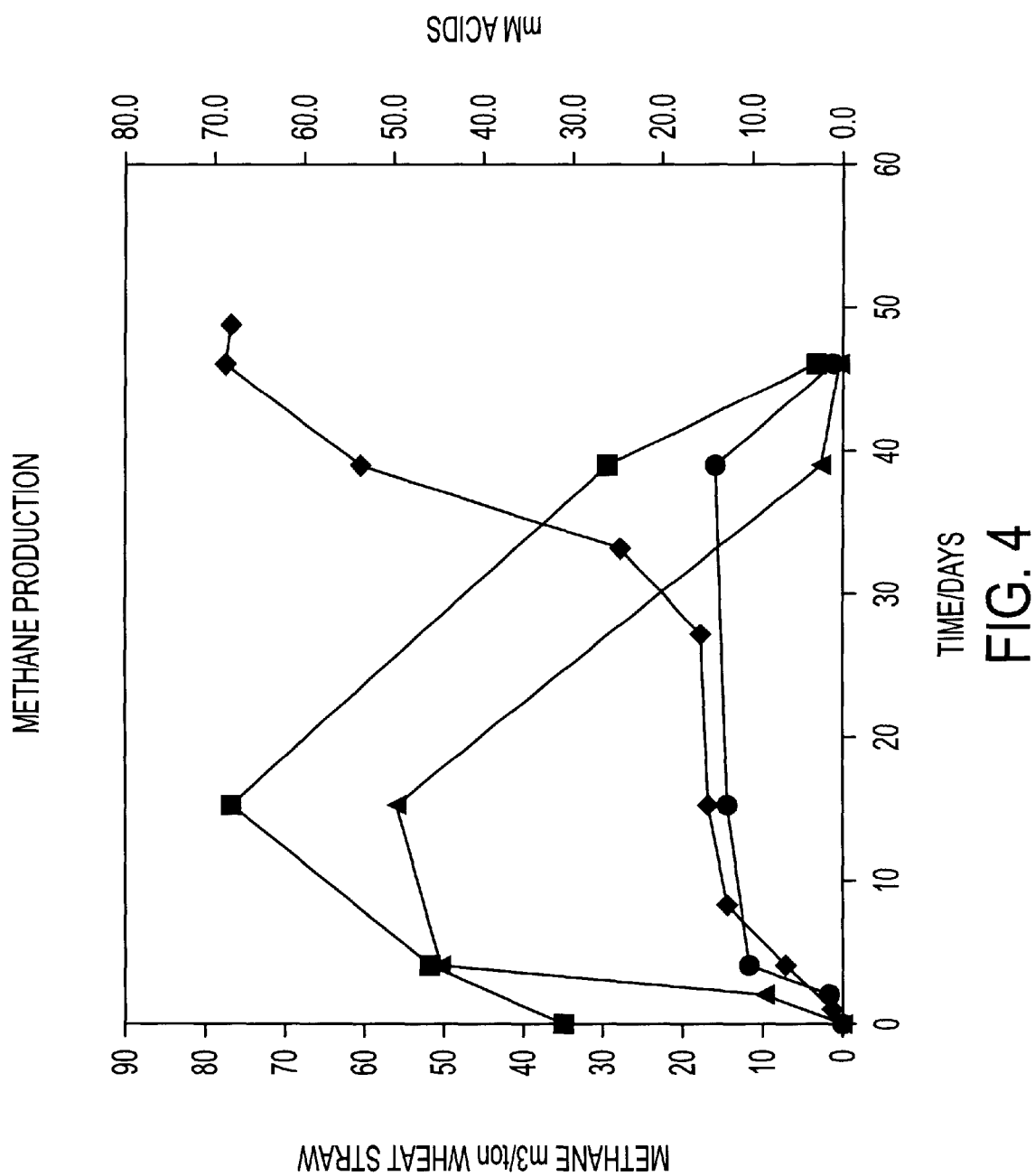

The invention is further illustrated in the following, non-limiting examples which were carried out on a laboratory pilot scale and which illustrate embodiments of the process according to the invention and the drawings wherein FIG. 1 shows a schematic drawing of a "Upflow Anaerobic Sludge Blanket" reactor (UASB reactor) useful for the anaerobic fermentation process in step (b) of the process of the present invention. The UASB reactor employs immobilised biomass in the form of a layer of sludge particles (1) at the bottom of the reactor. Liquid phase to be treated enters the reactor via one or more openings (A) at the bottom thereof and passes up through the biomass sludge particle layer. Near the top of the reactor is a screen or sieve (3) through which the treated, upwardly flowing liquid phase and the gas(es) generated by the anaerobic fermentation process can pass, but which prevents passage of granules. Some of the gas generated in the resulting anaerobic fermentation process (e.g. methane and, possibly, carbon dioxide in the case of the present invention) attaches itself temporarily to some of the particles of the microorganism sludge, increasing their buoyancy so that the particles in question (2) rise up through the liquid phase. When these particles strike the screen or sieve (3), the gas buoying them up is shaken off, whereupon the particles in question re-sediment at the bottom of the reactor. Treated liquid phase which has passed up through the screen or sieve (3) is drawn off at one or more liquid outlets (L), and the gas phase is drawn off at one or more gas outlets (G). In the case of generation of methane-containing gas (as in the process of the present invention), the gas may, for example, be stored in tanks or drawn off essentially continuously for production of heat or electricity;

FIG. 2 shows a schematic drawing of a wet-oxidation reaction vessel ("loop reactor") useful for the pre-treatment of the lignocellulosic material according to the present invention. A detailed description of the "loop reactor" in question may be found in Bjerre et al., 1996. The reactor comprises a steel container in the form of a cylinder having an inner diameter of about 11 cm and a height of 18 cm, and an externally placed steel tube with a length of 160 cm and an inner diameter of 22 mm. One end of the tube is welded to the outside of the bottom of the container, and the other end is welded to the outside of the lower part of the side of the container. In the bottom of the container, just above the tube connection, is a centrifugal impeller wheel which provides the recirculatory flow of the suspension/solution to be treated. The impeller wheel is driven by an electric motor via a magnetic coupling, the electric motor being placed outside the container. The top of the container is equipped with a steel lid which may be tightly bolted down against a flange assembly. The lid is equipped with an inlet valve for admitting air, oxygen or any other appropriate oxygen-containing gas (typically from a high-pressure gas cylinder) or other gas/vapour to the air-space (free volume) above the liquid phase in the loop reactor. The loop reactor has a capacity of 1 liter of liquid suspension, and the volume of the air-space (free volume) is 1 liter;

FIG. 3 shows a schematic drawing of the laboratory scale glass reaction vessel used in Example 1. The reaction vessel has a capacity of 200 ml and is surrounded by a heating jacket (1), through which water from a thermostatic water-bath may be circulated. An inlet tube which opens into the reaction vessel, and which passes through the lower part of the heating jacket, comprises a spiral portion (2) to prevent immobilised biomass from being exposed to a temperature shock from the incoming material to be treated by allowing the incoming material to more quickly attain substantially the temperature of the heating medium in the heating jacket. A ball (3) fits sealingly into the mouth of the inlet at the bottom of the reaction vessel and functions as a non-return valve to prevent the contents of the reaction vessel from escaping from the reaction vessel via the inlet tube. The reactor system as a whole is insulated with a 12 mm neoprene jacket. The top of the reaction vessel is equipped with tubes (4) which allow withdrawal of gas and liquid samples from the reaction vessel in the immediate vicinity of the outlet. A sieve or net (5) with a 1 mm mesh size is provided in the upper part of the reaction vessel to prevent any suspended, immobilised biomass from escaping from the reaction vessel; and FIG. 4 shows the methane production. Acetic acid, potential fermentation inhibitors and unfermented carbohydrates are converted to methane by a consortium of methanogenic Archaea, in a thermophilic anaerobic wastewater treatment step at 55° C.

EXAMPLE 1

Evaluation of the Results Obtained from Each Single Step in the Method for Processing Lignocellulosic Material 1.1. Materials and Methods 1.1.1 Reagents Unless otherwise indicated, reagents employed as described in the following are available from established suppliers of laboratory reagents.

1.1.2 Lignocellulosic Starting Material

The lignocellulosic material employed in the experiments described below was wheat straw harvested at Forskningscenter Rise (Rise National Laboratory) in 1997.

1.1.3 Reaction Vessel for Wet-Oxidative Pre-Treatment of Lignocellulosic Material The wet-oxidation reaction vessel employed was a recirculatory, laboratory scale reactor (in the following denoted the "loop reactor") capable of being pressurised with gas (FIG. 2). The loop reactor in question, which has previously been described by Bjerre et at., 1996

The loop reactor was heated by immersing it in a thermostatic bath of molten salt e.g. consisting of a 1:1 (w/w) mixture of anhydrous sodium nitrate and anhydrous sodium nitrite, and it was subsequently cooled by immersion in cold water. With respect to heating, the desired temperature is typically attained within about 3 minutes; with respect to cooling, about 1 minute is required to attain thermal equilibrium.

With the lid fitted and the valve closed, the loop reactor thus constitutes a closed-loop system in which a reaction mixture—in the present case in the form of a suspension of lignocellulosic biomass (wheat straw) in an aqueous medium under a pressure of oxygen—introduced into the container may be re-circulated for a chosen length of time at a chosen temperature.

1.1.4 Wet-Oxidative Pre-Treatment of Wheat Straw

Before performing wet oxidation, the straw was dried and comminuted by grinding to give fragments with a maximum length of 5 mm. The comminuted straw was mixed with deionized water (60 g straw per liter water), and sodium carbonate (6.5 g per liter water) was added. One liter of the mixture was transferred to the loop reactor, which was then closed and pressurised with oxygen gas (purity >99.9%) from a commercial gas cylinder to a pressure (initial pressure) of 12 bar. The reaction mixture was then subjected to re-circulatory wet oxidation at a temperature of 195° C. for a period of 10 minutes. After cooling, the contents of the reactor were poured into a 5 liter plastic container and stored at −20° C.

1.1.5 Growth Media

1) BA medium (synthetic medium): For preparing one liter of BA medium, the following components were first mixed in a conical flask:

| | |
|---|---|
| Deionized water (Milli-Q ™) | 916 ml |
| Solution A | 10 ml |
| Solution B | 2 ml |
| Solution C | 1 ml |
| Solution D | 1 ml |
| Sodium bicarbonate solution | 50 ml |
| Yeast extract | 1 g |

The mixture was then made anaerobic by bubbling with a gas mixture consisting of 80volume % nitrogen and 20 volume % carbon dioxide for 10 minutes. The measured pH was 6.9–7.0. The anaerobic mixture was then autoclaved at 140° C. for 20 minutes, whereupon the following were added under anaerobic conditions:

Vitamin solution (0.1 ml solution per 10 ml of medium)

Sodium sulphide solution (0.1 ml solution per 10 ml of medium).

The compositions of the various solutions employed were as follows:

Solution A (in grams per liter of solution, in deionized water): Ammonium chloride (100 g/l); sodium chloride (10 g/l); magnesium chloride hexahydrate (10 g/l); calcium chloride dihydrate (5 g/l).

Solution B (in deionized water): dipotassium hydrogen phosphate trihydrate (200 g/l).

Solution C (in deionized water): Resazurin sodium salt (0.5 g/l)

Solution D: the following components were introduced in the given amounts, added in the given order, into a 1000 ml volumetric flask:
deionized water (500 ml); boric acid (50 mg); zinc chloride (50 mg); copper(II) chloride dihydrate (38 mg); manganese(II) chloride dihydrate (41 mg); ammonium molybdate tetrahydrate (50 mg); aluminium chloride hexahydrate (90 mg); cobalt(II) chloride hexahydrate (50 mg); nickel(II) chloride hexahydrate (92 mg); ethylenediaminetetraacetic acid sodium salt (sodium EDTA; 500 mg); sodium selenite pentahydrate (100 mg).

To the volumetric flask was then added a solution prepared by mixing re-distilled water (1 ml), concentrated hydrochloric acid (1 ml) and ferrous chloride tetrahydrate (2000 mg) and allowing the mixture to stand until the ferrous chloride had dissolved. The volumetric flask was then filled to the mark with deionized water.

Sodium bicarbonate solution (in deionized water): anhydrous sodium bicarbonate (52 g/l).

Vitamin solution (in milligrams per liter of solution, in deionized water)(materials purchased from Sigma): biotin (vitamin H; 2 mg/l); folic acid (2 mg/l); pyridoxine hydrochloride (vitamin $B_6$; 10 mg/l); riboflavin (vitamin $B_2$; 5 mg/l); thiamine hydrochloride (vitamin $B_1$; 5 mg/l); cyanocobalamin (vitamin $B_{12}$; 0.1 mg/l); nicotinic acid (5 mg/l); p-aminobenzoic acid (5 mg/l); lipoic acid (thioctic acid; 5 mg/l); DL-pantothenic acid (5 mg/l). Since this solution is not stable towards autoclaving at 140° C., it was deoxygenated by bubbling with nitrogen gas, and then sterile filtered into anaerobic, autoclaved vials for storage until use.

Sodium sulphide solution: One liter of deionized water in an Erlenmeyer flask was deoxygenated by bubbling with nitrogen gas. A 25 g portion of sodium sulphide ($Na_2S \cdot 7$–$9H_2O$) was weighed out and added to the flask (in a hood) under continued bubbling with nitrogen. 20 ml aliquots of the solution were then transferred anaerobically to 100 ml vials, which were then autoclaved at 140° C.

2) Yeast growth medium (YM): this consisted of BA medium to which was were added extra vitamins, trace metals, yeast extract and Tween™80/ergosterol solution. Stock solutions of vitamins, trace elements and ergosterol/Tween™80 were prepared as follows:

Vitamin solution (100 ml):
(i) dissolve 5 mg biotin in 1 ml 0.1 M NaOH;
(ii) add the solution from (i) to about 80 ml water;
(iii) adjust pH of the solution from (ii) to 6.5 by addition of 1 M HCl/1 M NaOH;
(iv) dissolve the following vitamins one at a time, in the given order, in the solution from (iii) and adjust pH to 6.5 after each addition, as before:

| | |
|---|---|
| calcium pantothenate | 0.1 g |
| nicotinic acid | 0.1 g |
| myoinositol | 2.5 g |
| thiamine hydrochloride | 0.1 g |

-continued

| | |
|---|---|
| pyridoxin hydrochloride | 0.1 g |
| p-aminobenzoic acid | 0.02 g |

(v) add water to a total volume of 100 ml;
(vi) adjust pH to 6.5, as before;
(vii) sterile filter and divide into 5–10 ml portions, which are then stored in a refrigerator.

Trace element solution (100 ml):
(i) dissolve 1.5 g sodium EDTA in 50 ml water;
(ii) add 0.45 g zinc sulphate tetrahydrate to the solution from (i);
(iii) adjust pH of the solution from (ii) to 6.0 and then add the following in turn, adjusting pH to 6.0 after each addition:

| | |
|---|---|
| $MnCl_2 \cdot 2H_2O$ | 0.1 g |
| $CoCl_2 \cdot 6H_2O$ | 0.03 g |
| $CuSO_4 \cdot 5H_2O$ | 0.03 g |
| $Na_2MoO_4 \cdot 2H_2O$ | 0.04 g |
| $CaCl_2 \cdot 2H_2O$ | 0.45 g |
| $FeSO_4 \cdot 7H_2O$ | 0.3 g |
| $H_3BO_3$ | 0.1 g |
| KI | 0.01 g |

(iv) add water to a total volume of 100 ml;
(v) adjust pH to 4.0;
(vi) sterile filter and divide into 510 ml portions, which are then stored in a refrigerator.

Ergosterol/Tween™ 80 solution (200 ml):
(i) dissolve 1.5 g ergosterol in 64 ml boiling absolute ethanol;
(ii) add 67.2 g Tween™ 80 to the solution from (i) and adjust the volume to 200 ml by addition of absolute ethanol;
(iii) sterile filter.

1.1.6. Enzymatic Hydrolysis

Enzymatic hydrolysis was carried out in 1 liter infusion bottles with a total liquid volume of 500 ml. In order to provide optimal growth conditions for the microorganisms in the subsequent fermentation treatments (which were performed in the same bottles), wet-oxidised wheat straw (in the following sometimes referred to as WOS) was mixed with the various components of BA medium in such a way that the WOS liquid took the place of the deionized water which was otherwise employed in preparing BA medium. Each bottle was seated with a rubber septum and an aluminium sealing ring, and the bottles were then autoclaved at 120° C. for 1 hour. Subsequent additions to, and withdrawals from, the bottles took place under anaerobic and sterile conditions using hypodermic needles inserted through the rubber septum.

For enzymatic hydrolysis, 3.5 ml of Celluclast™ 1.5 L (Novo Nordisk A/S, Bagsvaerd. Denmark; a brochure providing further information on Celluclast™ is available on request from Novo Nordisk) per 500 ml WOS was added to the bottles, which were then incubated at pH 6.1 and 40° C. for 9 days.

1.1.7 Sugar Fermentation

After the hydrolysis treatment, yeast extract, extra vitamins, trace elements and ergostero/Tween™ 80 solution were added to all the bottles to provide optimum conditions for the sugar-fermenting microorganisms to be used in the fermentation process (viz. *Saccharomyces cerevisiae* and *Thermoanaerobacter mathranii* A3M4).

Microorganisms: the yeast *S. cerevisiae* (a mesophile) was employed to ferment glucose. Cells of *S. cerevisiae* were taken from the centre of a packet of baker's yeast and incubated in 20 ml serum bottles with YM medium at 30° C. for 24 hours; cells were then transferred to standard agar plates. After incubation, the plates were stored at 5° C. until colonies were removed and used for the fermentation experiments.

An adapted strain of the thermophilic bacteria *T. mathranii*, viz. *T. mathranii* A3M4 (Ahring et al. 1996) was employed to ferment xylose.

Fermentation: *S. cerevisiae* was added to the bottles, which were then incubated at 30° C. for 14 days; the bottles were then heated to 70° C., *T. mathranii* A3M4 was added, and the bottles were incubated at 70° C. for 10 days. In order to monitor the fermentation process, the pressure in the bottles was measured manometrically each day. Fermentation by the microorganism in question was taken to be complete when the pressure in the bottles was stable. Samples were taken upon completion of the yeast fermentation and the A3 M4 fermentation, respectively, in order to determine content of volatile fatty acids (VFA), ethanol content and total sugar content (by standard methods).

After completing the fermentation processes and taking appropriate samples, the bottles were opened and the contents [fermented, wet-oxidised straw (FWOS)] were centrifuged (in several batches) at 13200×G for 20 minutes at 4° C. to remove undegraded straw and other suspended material. The supernatants from the various centrifugation batches were pooled, mixed, poured into 1 liter plastic bottles and stored frozen at −20° C.; this supernatant phase is sometimes referred to in the following as $FWOS_s$. The precipitated phases (pellets) from the various centrifugation batches were treated likewise (product denoted $FWOS_p$).

1.1.8 "Upflow Anaerobic Sludge Blanket" (UASB) Reactor Experiments

These were carried out using a laboratory scale glass reactor with a capacity of 200 ml, the construction of the reactor being illustrated in FIG. 3. The reactor per se is surrounded by a heating jacket (1), through which, for example, water from a thermostatic water-bath may be circulated. Water with a temperature of 37° C. was employed in the experiments described here. An inlet tube which opens into the reactor, and which passes through the lower part of the heating jacket, comprises a spiral portion (2) to prevent immobilised biomass [containing the anaerobic organisms which result in methane formation in accordance with step (b) of a process of the invention] from being exposed to a temperature shock from the incoming material to be treated by allowing the incoming material to more quickly attain substantially the temperature of the heating medium in the heating jacket. A ball (3) fits sealingly into the mouth of the inlet at the bottom of the reactor per se and functions as a non-return valve to prevent the contents of the reactor from escaping from the reactor via the inlet tube. The reactor system as a whole is insulated with a 12 mm neoprene jacket.

Effluent (treated material) leaving the reactor is collected in an intermediate storage container, from which it is recirculated to the reactor in a ratio of 4:1 relative to fresh material which is to be treated. A peristaltic pump (Watson-Marlow) equipped with pump tubes of different diameter (and thereby different pumping capacity) is employed to pump both the recirculated, treated material and the fresh, incoming material and to ensure a constant ratio of recirculated material to fresh material irrespective of the speed of rotation of the peristaltic pump.

The top of the reactor is equipped with tubes (4) which allow withdrawal of gas and liquid samples from the reactor in the immediate vicinity of the outlet (the outlet being shown in FIG. 3 as a downwardly inclined tube stub at the upper right of the figure). A sieve or net (5) with a 1 mm mesh size is provided in the upper part of the reactor per se to prevent any suspended, immobilised biomass from escaping from the reactor.

The immobilised biomass (granules) employed in these experiments was supplied by Eerbeek BV in Holland and was taken from a mesophilic full-scale reactor which is used to purify wastewater from a paper mill. The biomass was stored at 5° C. prior to use in the reactor in the present experiments.

Gas pressure presses excess effluent from the reactor over into the effluent container, in which gas and liquid separate. The volume of gas may be measured using a meter based on the liquid-displacement principle (Angelidaki et al., 1992). The gas is not collected. Gas samples for determining the composition of the gas produced in the reactor are taken from a gas-withdrawal tube (4) immediately above the liquid level at the top of the reactor. This is done since it is to be expected that some methane production also occurs in the effluent receiver.

Before starting the reactor, the reactor system was filled with deoxygenated BA medium. 100 ml of immobilised biomass was introduced into the reactor, and 3 ml sodium sulphide solution (25 g/l) were added to reduce any oxygen in the reactor. To avoid inhibition of the immobilised biomass, the reactor was started using $FWOS_s$ diluted with BA medium to 25% (v/v) (see below) and with a residence time of 100 ml/day. Adaptation of the microorganisms in the biomass was monitored primarily by measuring VFA concentrations at the top of the reactor. Once the VFA content had stabilised, the concentration of $FWOS_s$ in the incoming material was gradually increased by steps of 20% (relative) until 100% $FWOS_s$ was attained. The residence time was then gradually reduced—likewise on the basis of VFA concentrations—until a residence time in the reactor of 200 ml/day was attained.

Preparation of $FWOS_s$ for start and operation of the reactor: The material for treatment was prepared in 1 liter infusion bottles autoclaved with pumping tubes. Dilutions of $FWOS_s$ were prepared by dilution with BA medium to the desired concentration; $FWOS_s$ was thawed, and ethanol was removed by heating at 85° C. The liquid was bubbled with air for 4 hours under reflux to reduce evaporation. During removal of ethanol, the remaining concentration was measured at intervals; evaporation was stopped when the remaining concentration of ethanol in the liquid was 5–10 mM. Evaporation was estimated on the basis of weight loss, and lost liquid volume was replaced by addition of deionized (Milli-Q™) water. The ethanol-depleted $FWOS_s$ where relevant diluted with BA medium was sterile filtered through a 0.2 μm filter into an autoclaved infusion bottle. The contents of the bottle were then deoxygenated by bubbling with 80/20 (v/v) nitrogen/carbon dioxide gas mixture for 15 minutes. A 40 ml sample was withdrawn, under sterile conditions, for determining VFA, ethanol content, chemical oxygen demand (COD) and total nitrogen, and its pH was measured. When replacing an almost empty infusion bottle with a fresh bottle, the medium remaining in the replaced bottle was also withdrawn for analysis. Samples taken from the infusion bottles were stored at −20° C. until analysed.

Monitoring. during upstart and subsequent operation of the reactor, gas production, gas composition and decrease in COD were measured in addition to VFA levels. In addition, samples were taken—after a minimum of 4 residence periods with maximum organic loading—from the inlet and the top of the reactor for gas-chromatographic determination of the degradation of various aromatic compounds. The samples were stored at −20° C. until analysed.

Analytical methods: Determination of dry matter content, organic matter, COD and Kjeldahl total nitrogen were performed according to Greenberg et al., 1992. Methane concentrations were determined gas-chromatographically using a FID detector. Concentrations of nitrogen, carbon dioxide and methane in the biogas produced in the reactor were determined gas-chromatographically using a thermal conductivity detector.

Concentrations of ethanol and VFA (acetate, propionate, butyrate and isobutyrate) was determined gas-chromatographically using a FID detector; samples for VFA determinations were first acidified by addition of 30µl of phosphoric acid (17%) per ml of sample and then centrifuged at 11000 rpm for 10 minutes.

Aromatic and pseudo-aromatic compounds of relevance as possible inhibitors of microorganisms (e.g. sugar-fermenting microorganisms), such as 2-furanoic acid, phenol, vanillic acid, homovanillic acid, acetovanillon, 4-hydroxybenzoic acid and others were determined by solid-phase extraction and gas chromatography using a FID detector, the solid-phase extractions were carried out at pH 2 and pH 7. The lower detection limit for the aromatic/pseudo-aromatic compounds was 1–2 ppm.

Total sugar determinations were performed after carrying out hydrolysis with strong acid (72% sulfuric acid) in a standard manner; concentrations of reducing sugars were then determined by the well-known dinitrosalicylic acid (DNS) method, using xylose as calibrant.

Potassium, Nitrate N and phosphate P levels were determined at the laboratory of the Danish Commercial Growers Association ("Dansk Erhvervsgartnerforening").

1.2 Results
1.2.1 Sugar Fermentation Results

In the wet-oxidative pre-treatment of wheat straw, described above, the straw was employed at a concentration of 60 g dried straw per liter water, corresponding to a theoretical dry matter content of 6% by weight (w/w). Before the fermentation experiments were performed, samples were taken in order to characterise the WOS. The results were as follows:

TABLE 1.1

Characterisation of WOS used in fermentation experiments

| | |
|---|---|
| Total sugars* | 31.8 ± 0.5 g/l |
| Dry matter | 55.4 ± 0.9 g/l |
| Organic matter | 44.5 ± 0.9 g/l |
| pH | 7.3 ± 0.2 |
| COD** | 61.4 ± 1.6 g/l |
| Kjeldahl N** | 0.12 ± 0.01 g/l |
| Acetate | 2.0 ± 0.1 g/l |

*Determined following strong acid hydrolysis and with xylose as standard.
**Standard deviation determined on the basis of two measurements.

Although acetate is clearly produced, its concentration is too low to cause appreciable inhibition of yeast, which has been reported (Taherzedeh et al., 1997) to be able to grow at an acetate concentration of 10 g acetate per liter at pH values as low as 4.5.

Based on the content of glucose and xylose in WOS, a "theoretical" (stoichiometric) yield of ethanol can be calculated as follows:

| | | |
|---|---|---|
| Glucose: | $C_6H_{12}O_6 \rightarrow 2C_2H_6O + 2CO_2$ | (molar ratio 1:2) |
| Xylose: | $3C_5H_{10}O_5 \rightarrow 5C_2H_6O + 5CO_2$ | (molar ratio 3:5) |

Expressed in grams ethanol per gram sugar this corresponds to a "theoretical" ethanol yield of 0.51 g ethanol/g glucose and 0.51 g ethanol/g xylose, i.e. 0.51 g ethanol/g total sugar. With an initial total sugar concentration of 31.8±0.5 g/l (Table 1.1), this corresponds to a theoretical maximum yield of 16.2±0.3 g ethanol/liter WOS.

Table 1.2 shows the average ethanol concentrations after fermentation of WOS with the two sugar-fermenting microorganisms in question.

TABLE 1.2

Ethanol formation during fermentation of wet-oxidised wheat straw (WOS)

| | S. cerevisiae fermentation | | T. mathranii A3M4 fementation | | Total |
|---|---|---|---|---|---|
| | g/l | % of total | g/l | % of total | g/l |
| Average | 5.3 ± 1.0 | 94% | 0.3 ± 0.2 | 6% | 5.6 ± 1.0 |

A comparison of the results in Table 1.2 with the "theoretical" ethanol yield shows that approximately 35% of the total sugar in the WOS were converted to ethanol in the present experiments. Ethanol (bioethanol) produced in this manner may, as already discussed, be isolated for use as a fuel, as a solvent or for other purposes.

1.2.2 Degradation of Organic Material in the UASB Reactor

Table 1.3 shows results obtained with 4 different samples (denoted R1–R4) of FWOS$_s$ after operation of the laboratory scale reactor for a period of more than 70 days.

TABLE 1.3

Results obtained with 4 different samples of fermented wet-oxidised wheat straw (FWOS$_s$) after operation of the laboratory scale reactor

| Sample | Taken (days)* | Resid. time (days) | Flow (ml/day) | COD in (g/l) | COD out (g/l) | COD reduction (% w/w) |
|---|---|---|---|---|---|---|
| R1 | 76 | 2.0 | 100 | 27.2 | 4.5 | 84 |
| R2 | 102 | 1.3 | 159 | 25.7 | 4.9 | 81 |
| R3 | 107 | 1.0 | 200 | 26.7 | 5.7 | 79 |
| R4 | 110 | 1.0 | 200 | 28.9 | 5.4 | 81 |

*Days after reactor start-up.

It may be seen that degradation of the organic matter (expressed as COD reduction) in the reactor is not affected by doubling the organic loading (from R1 to R4) as expressed by the ratio between COD in (in g/l) and the residence time (in days); this ratio is denoted OLR in the following.

The evolution of gas (biogas) in the reactor was also monitored. In a series of measurements made over the last approx. 60 days of operation of the reactor (days 53–110), rather close correlation between the amount of biogas produced per day and the OLR was observed; thus, the amount of biogas produced per day (liter/day) per COD unit introduced into the reactor per day (i.e. g COD/l/day) was roughly 0.1. The methane content of the gas produced was reasonably constant throughout the experiments, the average being 58.6±0.8% (v/v) methane.

1.2.3 Degradation of Microorganism-Inhibitory Substances

In order to investigate the degradation of various aromatic or pseudo-aromatic substances which had been found to be potential inhibitors of ethanol-producing microorganisms, samples R1–R4 referred to in connection with Table 3 were analysed before and after treatment in the UASB reactor with respect to the concentration of a number of such substances.

TABLE 1.4

Removal of inhibitors in UASB purification step

| Inhibitor | Inlet (ppm) | Outlet (ppm) | Reduction (%) |
|---|---|---|---|
| 2-Furoic acid | 5.61 | 0.00 | 100 |
| 4-hydroxybenzaldehyde | 3.46 | 0.35 | 90 |
| 4-hydroxybenzoic acid | 15.72 | 0.4 | 97 |
| Vanillic acid | 60.74 | 0.62 | 99 |
| Homovanillic acid | 25.08 | 0.69 | 97 |
| Syringic acid | 45.53 | 0.00 | 100 |
| Syringol | 7.43 | 0.96 | 87 |
| Acetovanillione | 5.40 | 1.13 | 79 |
| Acetosyringone | 28.11 | 0.97 | 97 |

As it is shown in Table 1.4, in the case of vanillic acid, homovanillic acid and acetovanillon, average initial concentrations of ca. 60 ppm, ca. 25 ppm and ca. 5 ppm, respectively, were found. After treatment in the reactor, the concentrations of all three species were reduced to a level around or under the detection limit (1–2 ppm) for the analysis. Similar results were obtained for syringic acid, acetosyringon and syringol, for which average initial concentrations of ca. 45 ppm, ca. 28 ppm and ca. 7 ppm, respectively, were found, whereas the concentrations after treatment in the reactor were all around or under the analytical detection limit of 1–2 ppm.

It is thus apparent that the anaerobic process taking place in a reactor of the type in question is capable of achieving (i) a very high degree of degradation of substances which, upon recycling of the liquid phase for reuse in a process according to the invention, might otherwise lead to inhibition of the fermentation of sugars in the manner described herein, and (ii) a high degree of removal of COD (organic matter in general) present in the material entering the reactor and formation of biogas which may be exploited, e.g., as a fuel.

The experiments and results thereof described above thus illustrate the workability and effectiveness of embodiments of a process according to the present invention.

Although the above Example illustrates the use of a wet oxidation treatment as a pre-treatment of the lignocellulosic biomass material, the present invention also encompasses the use of steam explosion as a pre-treatment. Table 1.5 shows the calculation of theoretical methane potential in wet oxidised wheat straw (WSWO) and steam exploded wheat straw (WSSE)—hydrolysates after ethanol fermentation steps.

TABLE 1.5

Theoretical Methane Potential - Calculations & Assumptions

| Hydrolysate | WSSE | WSWO | |
|---|---|---|---|
| INPUT | | | |
| Wheat straw conc. In hydrolysate | 60 | 60 | g/l |
| COD/TS-relationship | 1.1 | 1.1 | g/g |
| TS loss in pretreatment | 2% | 8% | g/g |

TABLE 1.5-continued

Theoretical Methane Potential - Calculations & Assumptions

| Hydrolysate | WSSE | WSWO | |
|---|---|---|---|
| Degree of COD conversion | 82% | 85% | g/g |
| Specific methane production | 0.35 | 0.35 | l-$CH_4$/g-COD |
| Hemicellulose in wheat straw | 28% | 28% | g/g |
| Cellulose in wheat straw | 37% | 37% | g/g |
| Hemicellulose recovery | 60% | 70% | g/g |
| Cellulose recovery | 90% | 80% | g/g |
| Glucose/cellulose relationship | 1.11 | 1.11 | g/g |
| Xylose/hemicellulose relationship | 1.14 | 1.14 | g/g |
| CALCULATIONS | | | |
| Glucose produced | 22.2 | 19.7 | g/l |
| Xylose produced | 11.5 | 13.4 | g/l |
| COD lost (sugars converted to ethanol) | 36 | 35 | gCOD/l |
| Initial COD in hydrolysate | 65 | 61 | gCOD/l |
| COD left for methane | 29 | 25 | gCOD/l |
| Methane production | 8.25 | 7.58 | l-$CH_4$/l-hydrolysate |
| Specific Methane production | 138 | 126 | $m_3$-$CH_4$/t-Straw |

These calculations are based on the following: Starting point is 60 g wheat straw per liter. The COD/TS relationship and COD removal rate for WSWO has been determined by BilCentrum, DTU. Value for COD removal rate for WSSE has been interpolated from batch experiments carried out at BilCentrum, DTU. Specific methane production, hemicellulose to xylose and cellulose to glucose is fixed stoichiometric values. Sugar compositions and recoveries have been determined by RISØ.

Calculations of methane production has been based on the fraction of the remaining COD after ethanol fermentations which can be converted to methane according to the determined conversion yields (Table 1.5). Based on sugar yields the COD lost to ethanol fermentation is determined and subtracted from the total COD present in the hydrolysates.

The methane production is then based on the remaining COD and the determined conversions of the specific effluents.

EXAMPLE 2

Evaluation of Degradation Products from Wet Oxidation of Lignocellulosic Material

2.1 Introduction

This example shows a study of the identification and quantification of the sugar yield and degradation products from wet oxidation of lignocellulosic material and to evaluate the fractionation of the cellulose and hemicellulose.

2.2 Summary of Experiments

Wet oxidation of wheat straw was performed with eight combinations of the four parameters; temperature, time, carbonate and oxygen. Two of the experiments were superior in obtaining solubilization of hemicellulose and lignin from the solid fraction, with high recoveries of the hemicellulose (52.0–56.5%) and the cellulose (99.7–99.8%). The solid fractions consisted of 67.5–65.8% cellulose, 7.6–10.4% hemicellulose and 4.8–5.6% lignin. The enzymatic convertibility of cellulose to glucose was 62.1–67.7%. The liquid fractions consisted of solubilized hemicellulose and low molecular weight degradation products such as carboxylic acids, monomeric phenols and furans. The degradation products in the solid and liquid fractions were related to the wet oxidation conditions: Reaction time, temperature and addition of carbonate and oxygen. Alkaline wet oxidation, e.g. addition of oxygen and carbonate, was important for the solubilization of lignin and hemicellulose from the solid fraction. A high enzymatic convertibility of the cellulose was correlated to a low lignin content in the solid fraction.

2.3 Materials and Methods

2.3.1 Materials

Wheat (*Triticum aestivum* L.) cv. Husar was grown and harvested at RisØ National Laboratory in 1997. The wheat straw was dried and ground to 5 mm. All solvents and chemicals were analytical grade and purchased from Fischer, Merck, Aldrich and Fluka.

2.3.2 Wet Oxidation Pre-Treatment

Wet oxidation was carried out in same loop-reactor as described above. Ground wheat straw (60 g) was mixed with 1 L water and $Na_2CO_3$ before adding oxygen pressure and heating the suspension. After cooling to about 25–30° C., the pre-treated wheat straw was divided by filtration into a solid fibre fraction and a liquid fraction.

2.3.3 Analyses of Solid Fibre Fraction

The solid fraction was dried to constant weight at 20° C. and 65% relative humidity. The solid fraction and starting material were analysed for its content of cellulose, hemicellulose, lignin and non cell wall material (NCWM) according to Goering and Soest (1970).

The enzymatic convertibility of the cellulose to glucose was determined by a Celluclast and Novozym 188(both from Novo Nordisk, Bagsvaerd) cellulase mixture (Schmidt and Thomsen, 1998).

2.3.4 Analyses of Liquid Fraction

The filtrate was analysed fresh (pH, TOC and furans) and then stored frozen (−20° C.) until further analyses. Total organic carbon was measured on a Shimadzu TOC-5000 with IR-detection after combustion at 680° C. (Pt-catalyst). Compensation for inorganic carbon was made by acidification with HCl. 5-Hydroxy-2-methylfurfural (5-HMF) and 2-furfural were determined in the fresh (filtered 0.45 μm) filtrate by HPLC (Nucleosil 5C-18, 25 mm column) with a linear eluent gradient of methanol (10–90%) at pH 3, using authentic compounds as calibration standards (Bjerre et al, 1996a). The hemicellulose was determined as the soluble sugars; glucose, xylose and arabinose after sulphuric acid hydrolysis (4% $H_2SO_4$, 121° C., 10 min), filtration and ion exchange purification by HPLC (Aminex HPX-87H) with 4 mM $H_2SO_4$ as eluent and 0.6 ml min$^{-1}$ flow at 63° C. (Bjerre et al, 1996b). Carboxylic acids were determined by ion chromatography on a Dionex 4000 i IC system, with Ionpac ICE-AS-6 column and 0.4 mM heptafluorobutyric acid as eluent at 1.0 ml min$^{-1}$ with combined conductivity and UV (204 nm) detection. Oxalic acid was determined on the same system but with Ionpac AS12A column and eluent 2.7 mM $Na_2CO_3$ and 0.3 mM $NaHCO_3$ at 1.5 ml min$^{-1}$.

2.3.5 Analysis of Phenols in Liquid Fraction

The liquid fraction or fermentation broth was centrifuged at 10,000 rpm for 10 minutes at 4° C. The supernatant was adjusted to pH 6.9–7.1 with 1M NaOH and to pH 1.9–2.1 with 1M HCl, respectively. The phenols and 2-furoic acid were isolated from the liquid fraction by solid phase extraction at pH 7 and pH 2. respectively, and were eluted with ethyl acetate (Isolute ENV+ 100 mg/1 mL, IST). The phenols, phenol aldehydes and phenol ketones were quantified from the pH 7 extract. The phenol acids and 2-furoic acid were quantified as their trimethylsitylated derivatives from the pH 2 extract. Samples from the pH 7 extraction were diluted with acetonitrile. Samples from the pH 2 extraction were diluted with acetonitrile and dried with $Na_2SO_4$. The supernatant was silylated in a mixture of BSTFA (N,O-Bis(trimethylsilyl) trifluoro-acetamide) and acetonitrile (1:5) at 70° C. for 30 minutes. The phenols were quantified by GC-MS and GC-FID analysis on a fused silica capillary column coated with a 0.25 μm film of 5% phenyl crossbond (HP-5, Agilent Technologies, U.S.A. or XTI-S, Restek Corp., U.S.A.), using authentic standards.

2.4. Results and Discussion

Wet Oxidation

This study is based on 8 experiments (a $2^{4-1}$ factorial design) for optimisation of alkaline wet oxidation of wheat straw (60 g L$^{-1}$) in relation to sugar yield and to fractionate the cellulose and hemicellulose. The temperature, reaction time, sodium carbonate and oxygen were the reaction parameters tested at two levels (Table 2.1). Each hydrolysate derived from the wet oxidation was divided by filtration into two fractions, a liquid, soluble fraction and a solid fibre fraction. The liquid fraction comprises hemicellulose and degradation products such as monomeric phenols, carboxylic acids and furans, whereas the solid fibre fraction comprises cellulose, hemicellulose, lignin and non-cell wall material.

TABLE 2.1

The statistical $2^{4-1}$ factorial design for wet oxidation applied for wheat straw (60 g kL$^{-1}$ straw).

| Factor | Parameter | Low level | High level | Units |
|---|---|---|---|---|
| A | Temperature | 185 | 195 | ° C. |
| B | $Na_2CO_3$ | 6.5 | 2 | g L$^{-1}$ |
| C | Oxygen | 6 | 12 | bar |
| D | Reaction time | 10 | 15 | minutes |

Relative to the starting material, straw, the solid fibre fractions contained 84–95.9% cellulose, 5.5–45.5 % hemicellulose, 28.1–67.5 % lignin and 25.9–44.7% non cell wall material (NCWM) (Table 2.2). The experimental conditions were optimal when a solid fraction with high cellulose content, low contents of lignin and hemicellulose and high enzymatic convertibility was produced. Also the recoveries of hemicellulose and cellulose should be high. Cellulose recoveries were more than 90 % in all the experiments, but the hemicellulose recoveries varied from 42 to 70%. A good fractionation of cellulose and hemicellulose with high cellulose convertibility to glucose was thus obtained in four of the experiments. But regarding the sugar recoveries only two experiments were optimal at the wet oxidation conditions: 15 minutes at 185° C. and 10 minutes at 195° C. with addition of 12 bar oxygen and 6.5 g L$^{-1}$ $Na_2CO_3$. The total amount of soluble sugars did not vary much and it did not correspond to the hemicellulose reduction in the solid fraction.

TABLE 2.2

Chemical composition, solubilized sugars, convertible cellulose and sugar recoveries of wet-oxidised wheat straw (60 g $L^{-1}$ straw).

| Initial or reaction products | | Temperature:<br>Time:<br>$O_2$-pressure:<br>$Na_2CO_3$: | 185° C.<br>10 min<br>6 bar<br>6.5 g $L^{-1}$ | 185° C.<br>10 min<br>12 bar<br>2 g $L^{-1}$ | 185° C.<br>15 min<br>6 bar<br>2 g $L^{-1}$ | 185° C.<br>15 min<br>12 bar<br>6.5 g $L^{-1}$ | 195° C.<br>10 min<br>6 bar<br>2 g $L^{-1}$ | 195° C.<br>10 min<br>12 bar<br>6.5 g $L^{-1}$ | 195° C.<br>15 min<br>6 bar<br>6.5 g $L^{-1}$ | 195° C.<br>15 min<br>12 bar<br>2 g $L^{-1}$ | Straw |
|---|---|---|---|---|---|---|---|---|---|---|---|
| Solid fraction | (g) | | 31.7 | 38.2 | 36.3 | 30.5 | 36.2 | 29.3 | 28.4 | 28.6 | 60 |
| NCWM | (% w/w) | | 13.9 | 17.1 | 16.1 | 14.7 | 18.6 | 15.7 | 13.7 | 21.8 | 25.1 |
| Hemicellulose | (% w/w) | | 13.8 | 20.0 | 14.7 | 10.4 | 12.3 | 7.6 | 8.0 | 3.2 | 27.9 |
| Lignin | (% w/w) | | 8.4 | 8.0 | 9.0 | 4.8 | 9.7 | 5.6 | 7.7 | 7.1 | 8.7 |
| Cellulose | (% w/w) | | 61.8 | 53.5 | 58.6 | 67.5 | 58.0 | 67.8 | 67.4 | 65.1 | 37.0 |
| Convertibility | (% w/w) | | 53.7 | 38.1 | 38.1 | 62.1 | 39.3 | 67.6 | 63.2 | 66.3 | 14.1 |
| Liquid fraction | | | | | | | | | | | |
| Glucose | (g/100 g) | | 3.6 | 4.3 | 4.0 | 2.9 | 3.8 | 2.6 | 2.8 | 3.2 | — |
| Xylose | (g/100 g) | | 8.7 | 6.3 | 8.7 | 9.6 | 10.2 | 9.9 | 10.1 | 10.5 | — |
| Arabinose | (g/100 g) | | 2.0 | 1.3 | 1.6 | 2.3 | 1.5 | 2.3 | 2.5 | 1.0 | — |
| Total sugars | (g/100 g) | | 14.3 | 11.9 | 14.2 | 14.8 | 15.5 | 14.8 | 15.4 | 14.7 | — |
| pH | — | | 7.7 | 4.7 | 4.8 | 6.0 | 4.7 | 5.9 | 6.1 | 3.8 | — |
| Recovery | | | | | | | | | | | |
| Hemicellulose | (%) | | 59.2 | 69.6 | 64.1 | 56.5 | 63.6 | 52.0 | 53.2 | 41.6 | 100 |
| Cellulose | (%) | | 94.3 | 102.4 | 105.7 | 99.7 | 103.9 | 99.8 | 93.3 | 91.7 | 100 |
| Total | (%) | | 79.2 | 88.3 | 87.8 | 81.2 | 86.5 | 76.9 | 76.1 | 70.1 | 100 |

The soluble fractions of wet-oxidised wheat straw consisted of a mixture of hydrolyzable sugars (7.1–9.2 g $L^{-1}$), carboxylic acids (1.9–7.2 g $L^{-1}$), phenols (ca. 0.14–0.20 g $L^{-1}$) and furans (0–0.09 g $L^{-1}$) (Table 2.3). The main phenols were vanillin, syringaldehyde, acetosyringone (4-hydroxy-3,5dimethoxyacetophenone), vanillic acid and syringic acid, occurring in 10–90 mg $L^{-1}$ levels. Under thermal and acidic conditions xylose will decompose to 2-furfural and glucose to 5-HMF. Experiments with a low level of carbonate addition produced both of these furans, where as experiments with a high level of carbonate did not. The experiment at the conditions; 15 minutes at 195° C. with 12 bar oxygen and 2 g $L^{-1}$ carbonate produced high level of furans and it also had the lowest final pH (Table 2.3). The results indicated that the sugar degradation products 2-furfural and 5HMF were favoured when pre-treatment was performed at low levels of carbonate addition, higher temperature and longer reaction times, with carbonate being the most important factor.

The formation of carboxylic acids was high in all experiments, formic acid and acetic acid being the main carboxylic acids. The formation of carboxylic acids was correlated with the removal of hemicellulose and lignin from the solid fraction (Tables 2.2 and 2.3). Thus the production of carboxylic acids seemed to be a result of lignin and hemicellulose degradation (Bjerre et al, 1996). Many non-volatile carboxylic acids were also identified as their trimethylsilyl derivatives by GC-MS from the freeze-dried liquid fractions: Succinic, glycolic, lactic, malic, maleic, fumaric, 2,3-dihydroxypropanoic and 2,4-dihydroxybutyric acid.

No phenols with aliphatic alcohol groups were observed except for 4-hydroxy-3-methoxy-phenethylene glycol. From the silylated extracts, several compounds could be identified: Phenol, guaiacol, syringol, 4-hydroxybenzaldehyde, vanillin, syringaldehyde, 2-furoic acid, 4-hydroxybenzoic acid, vanillic acid, syringic acid, p-coumaric acid, ferulic acid and 4-hydroxy-3methoxy-phenethylene glycol were verified by mass spectra and (when available) authentic standards. Due to keto-enol isomerisation of the phenolic ketones and formation of the enol TMS-ether upon treatment with BSTFA, the SPE extracts at pH 7 were analysed by GC-MS without derivatization. 4-hydroxyacetophenone, acetovanillone and 4-hydroxy-3,5-dimethoxyacetophenone were thus identified. 3,4,5-trimethoxy-acetophenone and 3,4,5-trimethoxybenzaldehyde were not identified.

TABLE 2.3

Compounds quantified (g or mg/100 g straw) in the liquid fraction of wet-oxidised wheat straw (60 g $L^{-1}$).

| Type | Compound | | Temperature:<br>Time:<br>$O_2$-pressure:<br>$Na_2CO_3$: | 185° C.<br>10 min<br>6 bar<br>6.5 g $L^{-1}$ | 185° C.<br>10 min<br>12 bar<br>2 g $L^{-1}$ | 185° C.<br>15 min<br>6 bar<br>2 g $L^{-1}$ | 185° C.<br>15 min<br>12 bar<br>6.5 g $L^{-1}$ | 195° C.<br>10 min<br>6 bar<br>2 g $L^{-1}$ | 195° C.<br>10 min<br>12 bar<br>6.5 g $L^{-1}$ | 195° C.<br>15 min<br>6 bar<br>6.5 g $L^{-1}$ | 195° C.<br>15 min<br>12 bar<br>2 g $L^{-1}$ |
|---|---|---|---|---|---|---|---|---|---|---|---|
| Sugars | Glucose | (g/100 g) | | 3.56 | 4.26 | 4.01 | 2.87 | 3.75 | 2.57 | 2.84 | 3.23 |
| | Xylose | (g/100 g) | | 8.71 | 6.31 | 8.66 | 9.58 | 10.19 | 9.94 | 10.06 | 10.51 |
| | Arabinose | (g/100 g) | | 2.04 | 1.33 | 1.56 | 2.32 | 1.51 | 2.33 | 2.52 | 0.98 |
| Acids | Formic acid | (g/100 g) | | 2.19 | 3.61 | 0.72 | 7.12 | 3.04 | 5.77 | 6.22 | 6.45 |
| | Acetic acid | (g/100 g) | | 1.92 | 1.68 | 1.52 | 2.57 | 1.61 | 2.12 | 2.60 | 2.27 |
| | Glycolic acid | (g/100 g) | | 0.49 | 0.58 | 0.59 | 1.51 | 0.73 | 1.45 | 2.02 | 1.16 |
| | Lactic acid | (g/100 g) | | 0.43 | n.d.[a] | 0.17 | n.d. | 0.22 | n.d. | 3.29 | n.d. |
| | Matic acid | (g/100 g) | | 0.10 | 0.21 | 0.19 | 0.31 | 0.17 | 0.27 | 0.24 | 0.23 |

TABLE 2.3-continued

Compounds quantified (g or mg/100 g straw) in the liquid fraction of wet-oxidised wheat straw (60 g $L^{-1}$).

| Type | Compound | | Temperature: 185° C. Time: 10 min $O_2$-pressure: 6 bar $Na_2CO_3$: 6.5 g $L^{-1}$ | 185° C. 10 min 12 bar 2 g $L^{-1}$ | 185° C. 15 min 6 bar 2 g $L^{-1}$ | 185° C. 15 min 12 bar 6.5 g $L^{-1}$ | 195° C. 10 min 6 bar 2 g $L^{-1}$ | 195° C. 10 min 12 bar 6.5 g $L^{-1}$ | 195° C. 15 min 6 bar 6.5 g $L^{-1}$ | 195° C. 15 min 12 bar 2 g $L^{-1}$ |
|---|---|---|---|---|---|---|---|---|---|---|
| | Citric acid | (g/100 g) | 0.07 | 0.00 | 0 | 0.09 | 0 | 0.03 | 0.07 | 0.07 |
| | Oxalic acid | (g/100 g) | 0.03 | 0.01 | 0.01 | 0.01 | 0 | 0.01 | 0.01 | 0.01 |
| | Succinic acid | (g/100 g) | 0.83 | 0.26 | 0.24 | 0.40 | 0.25 | 0.38 | 0.47 | 0.41 |
| Furans | 5-Hydroxymethylfurfural | (mg/100 g) | 0 | 0 | 0 | 0 | 0 | 0 | 0 | 15 |
| | 2-Furfural | (mg/100 g) | 0 | 3 | 0 | 0 | 32 | 0 | 0 | 135 |
| | 2-Furoic acid | (mg/100 g) | 0 | 3 | 5 | 5 | 6 | 11 | 7 | 16 |
| Phenols | Phenol | (mg/100 g) | 2 | 1 | 1 | 3 | 1 | 5 | 5 | 2 |
| | Guaiacol | (mg/100 g) | 17 | 3 | 6 | 5 | 9 | 19 | 32 | 8 |
| | Syringol | (mg/100 g) | 15 | 1 | 2 | 0 | 6 | 6 | 13 | 5 |
| | 4-Hydroxy benzaldehyde | (mg/100 g) | 12 | 35 | 36 | 22 | 39 | 35 | 25 | 55 |
| | Vanillin | (mg/100 g) | 7 | 59 | 66 | 15 | 74 | 54 | 28 | 89 |
| | Syringaldehyde | (mg/100 g) | 1 | 23 | 35 | 1 | 50 | 41 | 3 | 69 |
| | 4-Hydroxy acetophenone | (mg/100 g) | 2 | 3 | 4 | 5 | 5 | 7 | 6 | 8 |
| | Acetovanillone | (mg/100 g) | 6 | 7 | 8 | 8 | 10 | 15 | 14 | 14 |
| | Acetosyringone | (mg/100 g) | 45 | 40 | 46 | 31 | 56 | 65 | 70 | 66 |
| | 4-Hydroxy benzoic acid | (mg/100 g) | 1 | 10 | 6 | 18 | 4 | 16 | 6 | 11 |
| | Vanillic acid | (mg/100 g) | 3 | 39 | 37 | 46 | 28 | 112 | 40 | 78 |
| | Syringic acid | (mg/100 g) | 5 | 12 | 23 | 8 | 28 | 37 | 48 | 46 |
| | p-Coumaric acid | (mg/100 g) | 12 | 18 | 24 | 6 | 24 | 18 | 6 | 12 |
| | Ferulic acid | (mg/100 g) | 8 | 5 | 12 | 5 | 16 | 17 | 6 | 14 |
| | TOTAL AMOUNT | (g/100 g) | 20.49 | 18.52 | 17.97 | 26.95 | 21.86 | 25.31 | 30.63 | 25.97 |

Important observations can be made comparing the two experiments at the conditions: 10 minutes at 195° C. with oxygen and carbonate addition at low levels and high levels, respectively. The hemicellulose and lignin content in the solid fraction was low when oxygen and carbonate was added at the high level, and high when the oxygen and carbonate was added at the low level (Table 2.2). The total content of phenols was about the same, but with high oxygen and carbonate levels the total content of carboxylic acids was very high. This indicated that the phenols to some extent were converted to carboxylic acids during the wet oxidation process. Wet oxidation of model aromatic compounds like phenol and quinolin resulted in quantitative degradation to carboxylic acids.

EXAMPLE 3
Evaluation of the Potential Inhibitors at Various Steps of the Process for Converting Lignocellulosic Biomass Material
3.1 Material and Methods
3.1.1 Pre-Treatment—Wet Oxidation Wet oxidation (WO) was carried out in a 2-L loopreactor constructed at RisØ National Laboratory (Bjerre et al., 1996). Pre-treatment conditions for fermentation substrate was 10 minutes wet oxidation at 195° C., 6.5 g/L $Na_2CO_3$ and 12 bar $O_2$. Ground wheat straw (5 mm) (60 g) was nixed with 1-L water and $Na_2CO_3$ before adding oxygen pressure and heating the suspension. After cooling to below 30° C., the whole slurry of pre-treated wheat straw was removed from the reactor by suction. The composition of wheat straw was determined as previously described (Ahring et al., 1996). Pretreated wheat straw consisted of 34.6 g/l cellulose, of which 20.8 g/l could be converted to glucose (67 °/a enzymatic convertibility) by a CelluClast® and Novozymo 188 cellulase mixture (Schmidt et al., 1998), kindly provided by Novo Nordisk A/S, Denmark. No monomeric xylose was seen after wet oxidation. Upon weak acid hydrolysis of the pretreated wheat straw (performed as described by (Ahring et al., 1996)) the concentration of monomeric xylose was 6 g/l.

3.1.2 Enzymatic Hydrolysis

It was previously shown (Ahring et al., 1998) that hemicellulose hydrolysate treated with CelluClast® increased the availability of the hemicellulose substrate. Thereby, the ethanol production with *Thermoanaerobacter mathranii* A3 was largely increased. In the wet oxidised wheat straw medium, pH was adjusted to 7.0 before autoclaving. To the medium was then added 1% v/v CelluClast® (corresponding to 17.5 FPU/g cellulose, FPU Filter Paper Units) a commercially available broad spectered crude cellulase with some xylanase activity from *Trichoderma reesei*. This mixture was incubated for 24 hours at 40° C. and pH 7.0.

3.1.3 Ethanol Fermentation—Microorganisms and Medium Used

*Thermoanaerobacter mathranii* A3M4

A mutant of *Thermoanaerobacter mathranii* strain A3 originally isolated from an Icelandic hot-spring as described by (Sonne-Hansen et al., 1993), was used in the experiments. *T. mathranii* A3 has been described by (Larsen et al., 1997). All fermentation's were performed at 70° C. and pH 7.0. A3M4 was obtained essentially as described by (Ahring et al., 1996).

*Saccharomyces cerevisiae*

Bakers yeast was purchased from The Danish Alcohol Producer. Cells were taken from the middle of the package and transferred to a 20 ml serum bottle containing YM, incubated for 24 hours and plated on standard agarose plates. All yeast cultivations were performed at 30° C. and pH 6.0.

Medium for *Saccharomyces cerevisiae*

The composition of the basic yeast medium (YM) was as follows: all in g/l $(NH_4)_2SO_4$ 5.0, $MgSO_4$, $7H_2O$ 0.5, $KH_2PO_4$ 3.0. All in mg/l vitamins Biotin 0.050, Ca-pantothenate 1.0, Myo-inositol 25.0, Thiamin, HCL 1.0, Pyridoxine, HCL 1.0, Para-aminobenzoic acid 0.2. All in mg Trace metals EDTA 15.0, $ZnSO_4$, $7H_2O$ 4.5, $MnCl_2$, $2H_2O$ 1.0, $CoCl_2$, $6H_2O$ 0.3, $CuSO_4$, $5H_2O$ 0.3, $Na_2MoO_4$, $2H_2O$ 0.4, $CaCl_2$, $2H_2O$ 4.5, $FeSO_4$, $7H_2O$ 3.0, $H_3BO_3$ 1.0, Kl 0.1. Ergosterol 10 mg/l, Tween 80 84 mg/l. The basic medium was gassed for 20 min with a $N_2/CO_2$ (4:1) atmosphere and pH adjusted to 6.0 before autoclavation.

Stock Solutions

Vitamin and trace metal solutions were prepared as 1000× stock solutions. Ergosterol and Tween 80 were prepared as a 1250×stock solution dissolved in 96% ethanol. All stock solutions were gassed for 20 min with a $N_2/CO_2$ (4:1) atmosphere, sterile filtered and added after autoclavation.

For inoculation a fresh colony was picked and transferred to a serum bottle containing YM, the bottle was closed, and incubated overnight at 30° C. on a horizontal shaker at 200 rotations/min. 10% overnight culture was then transferred to anaerobic YM and again incubated overnight. The culture was used as inoculum in the fermentation experiments. Optical density, OD578 in bottles used for inoculum was 2.0.

Medium for *Thermoanaerobacter mathranii* A3M4

BA medium as previously described by (Angelidaki et al., 1990) amended with 1 g/l yeast extract (Difco) but with no cysteine, was used for the cultivation of *Thermoanaerobacter mathranii* strain A3M4. The medium was reduced with 0.25 g/l sodium sulphide. The initial D-xylose concentration was 5 g/l and incubation was at 70° C. and pH 6.8. An overnight culture grown on BA with 5 g/l xylose was used as inoculum in the fermentation experiments. $OD_{578}$ in bottles used for inoculum was 0.8.

Combined Media

The combined s synthetic medium (for cultivation of both *S. cerevisiae* and *T. mathranii*), CSM, consisted of BA medium plus stock solutions as used for the yeast medium: trace metals, vitamins and ergosterol/tween80. The medium was supplemented with 12 g/l glucose and 5 g/l xylose. Optical density ($ODs_{578}$) was used for evaluating growth. The combined wheat straw medium, CWSM, contained wet oxidised wheat straw supplemented with the same concentrations of salts, trace metals, vitamins arid ergosterol/tween80as the CSM, but with no addition of glucose and xylose.

Ethanol Fermentation

The ethanol fermentation was performed in 300 ml serum bottles containing 100 ml medium. The combined wet oxidised wheat straw medium (CWSM) was pre-incubated with CelluClast as described above. pH was adjusted to 6.0, inoculated with *Saccharomyces cerevisiae* to a calculated ODS78 of 0.05 and incubated at 30° C. on a horizontal shaker at 200 (rotations/min) for five days. After termination of the yeast fermentation, the suspension was adjusted to pH 6.8, with 1% NaOH, added from a sterile anaerobic stock solution before 5% *Thermoanaerobacter mathranii* A3M4 inoculation culture was added (final concentration). The thermophiiic fermentation was performed at 70° C. without shaking for five days.

3.1.4 Distillation

After fermentation with *Thermoanaerobacter mathranii* A3M4, ethanol from the bottles containing CWSM enzymatically hydrolysed with CelluClast was distilled off. A 30 cm vertical water cooler system was mounted, heated to 70° C. and flushed with $N_2/CO_2$ (4:1) for 1.5 hours to ensure that the ethanol was removed.

3.1.5 Methane Production

*Methanogenic inoculum* used was taken from an anaerobic continuously stirred tank reactor operating at 55° C., with household waste as substrate.

The remaining suspension was then inoculated with 10% v/v of anaerobic inoculum and incubated at 55° C. without shaking.

3.1.6 Analytical Methods

Samples (1 ml) from the fermentation broth were acidified by 30 µL 17% phosphoric acid for quantification of ethanol and acetic acid. The samples were analysed on a HP5890 Series II gas chromatograph with flame ionisation detection and a silica capillary column (cross linked polyethylene glycol-TPA, 30 m, 0.53 mm). Methane was measured as described by (Angelidaki, L, 1990). COD was measured according to American standards. $OD_{578}$ measurements were performed an a spectrophotometer (Milton Ron) at 578 nm. Ethanol volumetric productivity was determined as mM EtOH produced per hour by linear regression through data points at mid logarithmic growth (between 4 and 12 hours).

3.1.7 Analysis of Phenols Hydrolysate

The liquid fraction or fermentation broth was centrifuged at 10.000 rpm for 10 minutes at 4° C. The supernatant was adjusted to pH 6.9–7.1 with 1M NaOH and to pH 1.9–2.1 with 1 M HCl, respectively. The phenols and 2-furoic acid were isolated from the liquid fraction by solid phase extraction at pH 7 and pH 2, respectively, and were eluted with ethyl acetate (Isolute ENV+ 100 mg/1 ml, IST). The phenols, phenol aldehydes and phenol ketones were quantified from the pH 7 extract. The phenol acids and 2-furoic acid were quantified as their trimethylsilylated derivatives from the pH 2 extract. Samples from the pH 7 extraction were diluted with acetonitrile. Samples from the pH 2 extraction were diluted with acetonitrile and dried with $Na_2SO_4$. The supernatant was silylated in a mixture of BSTFA (N,O-Bis(trimethylsilyl) trifluoro-acetamide) and acetonitrile (1:5) at 70° C. for 30 minutes. The phenois were quantified by GC-MS and GC-FID analysis on a fused silica capillary column coated with a 0.25 µm film of 5% phenyl crossbond (HP-5, Agilent Technologies, U.S.A. or XTI-S, Restek Corp., U.S.A.), using authentic standards.

3.3. Results

The fermentation of wet oxidised wheat straw to ethanol resulted in 138.7 mM ethanol produced from 60 g/l wheat straw. 110 mM ethanol was produced by *S. cerevisiae* and 28.7 mM produced by *T. mathranii*. In addition 10.1 mM acetic acid was produced during the thermophilic xylose fermentation step. The effluent from ethanol production, after distillation, was converted to methane by a consortium of thermophilic methanogenic Archaea. 77.6 $m^3$ methanelton wheat straw was produced (FIG. 4) and during the methanogenic step 71% of the COD content was removed.

The fate of potential fermentation inhibitors produced during wet oxidation of wheat straw was monitored at key points in the ethanol process. From Table 3.1 it can be seen that the phenolic aldehydes 4-hydraxy benzaldehyde and vanillin were both almost completely metabolised by *S. cerevisiae*. Syringic acid was also partly metabolised by *S. cerevisiae*. The concentration of syringic acid, however, reverted to its initial level after xylose fermentation by *T. mathranii* indicating formation of syringic acid by the thermophile. In addition there was an increase in the concentration of 4-hydroxybenzoic acid after the thermophilic fermentation step. None of the other phenolic compounds

TABLE 3.1

Potential fermentation inhibitors measured at key points in the process

| Phenols mg/l | S. cerevisiae, start | S. cerevisiae, end T. mathranii, start | T. mathranii, end, Ww-treatment, start | Ww-treatment, end |
|---|---|---|---|---|
| phenol | 4.5 | 3.9 | 3.8 | 0.9 |
| guaiacol | 8.5 | 8.0 | 8.2 | 0.0 |
| syringol | 2.3 | 2.8 | 3.6 | 0.0 |
| 4-hydroxy | 13.7 | 0.9 | 0.6 | 0.0 |

TABLE 3.1-continued

Potential fermentation inhibitors measured at key points in the process

| Phenols mg/l | S. cerevisiae, start | S. cerevisiae, end T. mathranii, start | T. mathranii, end, Ww-treatment, start | Ww-treatment, end |
|---|---|---|---|---|
| benzaldehyde vanillin | 10.6 | 1.9 | 1.1 | 0.1 |
| syringaldehyd | 3.6 | 3.2 | 2.6 | 0.3 |
| 4-hydroxy acetophenone | 2.8 | 2.5 | 2.7 | 0.2 |
| acetovanillone | 5.0 | 5.0 | 4.9 | 0.2 |
| acetosyringone | 17.4 | 19.0 | 20.0 | 1.9 |
| 2-furoic acid | 7.2 | 6.2 | 6.5 | 0.0 |
| 4-hydroxy benzoic acid | 23.7 | 22.8 | 26.0 | 0.0 |
| vanillic acid | 32.3 | 31.2 | 30.6 | 0.1 |
| syringic acid | 20.2 | 16.1 | 19.0 | 0.1 |
| p-coumaric acid | 5.0 | 5.1 | 4.7 | 0.0 |
| ferulic acid | 2.1 | 3.4 | 3.0 | 0.2 |
| TOTAL phenols | 158.8 | 131.9 | 137.4 | 4.0 |
| Acetic acid | 23.5 | 23.0 | 33.2 | 1.8 | alcohols, aldehydes, pentose degradation products, ketones or acids were metabolised by *S. cerevisiae* or *T. mathranii*. As a consequence of conversion of 4-hydroxy benzaldehyde and vanillin by *S. cerevisiae*, the total concentration of phenolic compounds measured decreased during the mesophilic hexose fermentation step. Of the small carboxylic acids acetic acid monitored, of which 23.5 mM was produced during pre-treatment of wheat straw and an additional 10.1 mM was formed during mixed acid fermentation by *T. mathranii*. In the thermophilic anaerobic wastewater treatment step all phenolic compounds, pentose degradation products and acetic acid are converted into methane. Of initially 158.8 mg/l phenolic compounds, 40 mg/l still remains after wastewater treatment and of 33.2 mM acetic acid, 1.8 mM was left unmetabolized. This corresponds to 97% removal of phenols and 94% removal of acetic acid.

These results clearly show that it is possible to reduce the level of inhibitory substances in the wastewater obtained from an ethanol fermentation to a level which allows all or part of the treated wastewater to be recycled into the process without any substantial inhibition of the pretreatment of the lignocellulosic biomass or of the subsequently hydrolysis or the fermentation of sugars.

REFERENCES

Ahring, B. K., Jensen, K., Nielsen, P., Bjerre, A. B. & Schmidt, A. S. 1996. Pretreatment of wheat straw and conversion of xylose and xylan to ethanol by thermophilic anaerobic bacteria. 58:107–113.

Angelidaki et al., 1992, Biotechnology and Bioengineering 39:351–353.

Angelidaki, I., Petersen, S. P. & Ahring, B. K. 1990. Effects of lipids on the anaerobic digestion and reduction of lipid inhibition upon addition of bentonite. Applied Microbiology Biotechnology 33:469–472.

Bailey & Ollis. 1986. Biochemical Engineering Fundamentals, McGraw-Hill, International Edition, Chemical Engineering Series.

Goering and Soest. 1970. Forage fiber analyses (apparatus, reagents, procedures, and som applications), pp. 1–20. In: Agricultural handbook No 379. Agricultural Research Services, USDA, Washington D.C.

Larsen, L., Nielsen, P., & Ahring, B. K. 1997. *Thermoanaerobacter mathranii* sp. nov., an ethanol producing extremely thermophilic bacterium from a hot-spring in Iceland. Arch Microbiol 168: 114–119.

Puls, J. 1993. Substrate analysis of forest and agricultural wastes, pp. 13–32. In: J. N. Saddler (ed.), Bioconversion of forest and agricultural plant residues. CAB International, Wallingford, UK.

Saddler, J. N., Ramos, L. P., Breul, C. 1993. Steam pretreatment of lignocellulosic residues, pp. 73–91. In: J. N. Saddler (ed.), Bioconversion of forest and agricultural plant residues. CAB International, Wallingford, UK.

Schmidt, A. S. & Ahring, B. K. 1996. Biotechnology and Bioengineering 49(3):229–246.

Schmidt, A. S. & Thomsen, A. B. 1998. Optimization of wet oxidation pretreatment of wheat straw. Biores. Biotechnol. 64: 139–151.

Sonne-Hansen, J., Mathrani, I. M. & Ahring, B. K. 1993. Xylanolytic anaerobic thermophiles from Icelandic hot-springs. Applied Microbiology and Biotechnology, 38:537–541.

Taherzedeh, M. J., Niklasson, C., & Lidén, G. 1997. Acetic acid—friend or foe in anaerobic batch conversion of glucose to ethanol by *Saccharomyces cerevisiae*. Chem Eng Sci 52:2653–2659.

What is claimed is:

1. A process for continuously converting solid lignocellulosic biomass material into ethanol wherein all or part of process water is recycled, the process comprising the steps of:
   (i) providing an aqueous slurry of the biomass material;
   (ii) subjecting, in a reaction vessel, said aqueous slurry to elevated temperature conditions, to an oxygen enriched atmosphere or to a combination of elevated temperature conditions and an oxygen enriched atmosphere, to obtain a slurry in which at least partial separation of the biomass material into cellulose, hemicellulose and lignin has occurred;
   (iii) subjecting the slurry resulting from step (ii), an aqueous phase of the slurry resulting from step (ii) or a combination of the slurry resulting from step (ii) and an aqueous phase of the slurry resulting from step (ii) to a treatment resulting in at least partial hydrolysis of the cellulose and hemicellulose to obtain a slurry, an aqueous phase, or a combination of the slurry and the aqueous phase, comprising an amount of microbially fermentable sugars that permits the slurry, the aqueous phase or the combination of the slurry and the aqueous phase to be used as an ethanol fermentation medium
   (iv) subjecting the slurry, the aqueous phase or the combination of the slurry and the aqueous phase of step (iii) to at least one ethanol fermentation step;
   (v) separating the ethanol from the fermentation medium resulting from step (iv), resulting in a fermentation wastewater effluent containing a level of inhibitory substances that, if present in any of the preceding steps (ii) to (iv) would be rate limiting or inhibitory;
   (vi) subjecting said wastewater effluent to a treatment whereby the level of the inhibitory substances is reduced to a level that, if the wastewater effluent is introduced into any of the preceding steps (ii) to (iv) is not rate limiting or inhibitory;
   (vii) introducing all or part of the thus treated wastewater effluent into any of the preceding steps (ii) to (iv); and
   (viii) continuously repeating steps (i) to (vii).

2. A process according to claim 1 wherein the treatment of step (vi) is an anaerobic fermentation process.

3. A process according to claim 2, wherein the treatment of step (vi) is performed by an acetogenic microorganism.

4. A process according to claim 1 wherein the treatment of step (vi) is performed using a methane producing microorganism.

5. A process according to claim 4, wherein said methane producing microorganism is selected from the group consisting of species of Methanobacterium, Methanobrevibacter, Methanothermus, Methanococcus, Methanomicrobium, Methanogenium, Methanospirillum, Methanoplanus, Methanosphaera, Methanosarcina, Methanolobus, Methanoculleus, Methanothrix, Methanosaeta, Methanopyrus and Methanocorpusculum.

6. A process according to claim 1 wherein in step (ii) the aqueous slurry is subjected to alkaline conditions.

7. A process according to claim 1, wherein a carbohydrase enzyme (EC 3.2) is used in the partial hydrolysis of step (iii).

8. A process according to claim 7, wherein said carbohydrase enzyme is selected from the group consisting of cellulases (EC 3.2.1.4); β-glucanases; glucan-1, 3-β-glucosidases (exo-1, 3-β-glucanases, EC 3.2.1.58); endo-1, 3(4)-β-glucanases (EC 3.2.1.6); xylanases; endo-1, 4-β-xylanases (EC 3.2.1.8); and pectinases (EC 3.2.1.15).

9. A process according to claim 1, wherein the slurry, the aqueous phase or the combination of the slurry and the aqueous phase obtained in step (iii) comprises, calculated on the total content of carbohydrate, at least 40% fermentable sugars.

10. A process according to claim 1, wherein the ethanol fermentation of step (iv) is performed by a fermenting microorganism selected from the group consisting of *Saccharomyces cerevisiae*, Pichia spp., Thermoanaerobacter spp. and Zymomonas spp.

11. A process according to claim 1, wherein said lignocellulosic biomass material is selected from the group consisting of garden refuse, comminuted wood, straw, hay, fruit hulls and seed hulls.

12. A process according to claim 1, wherein said lignocellulosic biomass material is selected from the group consisting of oat straw, barley straw, wheat straw, rye straw, oat hulls, barley hulls, wheat hulls, rye hulls, rice hulls, millet hulls, sorghum hulls, maize hulls, rape-seed hulls, cotton-seed hulls and sunflower seed hulls.

13. A process according to claim 1, wherein in step (ii) the aqueous slurry is further subjected to a wet oxidation treatment.

14. A process according to claim 1 wherein in step (ii) the aqueous slurry is further subjected to a steam explosion treatment.

15. A process according to claim 1, wherein step (ii) is performed as a batch process in a closed, pressurizable reaction vessel having a free volume for containing oxygen-containing gas or water vapour with or without further gasses.

16. A process according to claim 1, wherein step (ii) is performed as a batch process in a closed, pressurizable reaction vessel with recirculation of the reaction mixture.

17. A process according to claim 1, wherein step (ii) is performed as a continuous process in an essentially tubular reactor.

18. A process according to claim 1, wherein the reaction vessel employed in step (ii) has an initial partial pressure of oxygen in the range of 0.5–35 bar.

19. A process according to claim 1, wherein step (ii) is performed at a temperature which is more than 100° C.

20. A process according to claim 1, wherein step (ii) is performed at a temperature in the range of 120–240° C.

21. A process according to claim 20, wherein step (ii) is performed at a temperature which is less than 200° C.

22. A process according to claim 20, wherein step (ii) is performed at a temperature in the range of 180–210° C.

23. A process according to claim 1, wherein step (ii) is performed for a period of time in the range from 1 minute to 1 hour.

24. A process according to claim 1, wherein at least 60% of the hemicellulose, cellulose and lignin contained in the aqueous slurry of step (i) is recovered after step (ii).

25. A process according to claim 1, wherein the level of inhibitory substances in the fermentation wastewater effluent is reduced by at least 80% in step (vi).

26. A process according to claim 1, wherein at least 5% of the wastewater effluent treated in step (vi) is introduced into any of the preceding steps (i) to (iv).

* * * * *